US006680167B2

(12) United States Patent
Bertin et al.

(10) Patent No.: US 6,680,167 B2
(45) Date of Patent: Jan. 20, 2004

(54) MOLECULES OF THE CARD-RELATED PROTEIN FAMILY AND USES THEREOF

(75) Inventors: John Bertin, Watertown, MA (US); Moses V. Chao, New York, NY (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 37 days.

(21) Appl. No.: 09/748,537

(22) Filed: Dec. 26, 2000

(65) Prior Publication Data

US 2002/0061833 A1 May 23, 2002

Related U.S. Application Data

(63) Continuation-in-part of application No. 09/099,041, filed on Jun. 17, 1998, now Pat. No. 6,340,576, which is a continuation-in-part of application No. 09/019,942, filed on Feb. 6, 1998, now Pat. No. 6,033,855.

(51) Int. Cl.$^7$ ............................ C12Q 1/68; C01N 33/53
(52) U.S. Cl. ............................... 435/4; 436/6; 436/7.1; 436/375; 436/455; 536/23.1
(58) Field of Search ........................... 435/6, 375, 455, 435/7.1, 4; 536/23.1

(56) References Cited

U.S. PATENT DOCUMENTS

| 6,033,855 A | 3/2000 | Bertin | 435/6 |
| 6,340,576 B1 | 1/2002 | Bertin | 435/69.1 |

FOREIGN PATENT DOCUMENTS

| DE | 19813839 | 9/1999 |
| WO | WO 98/55507 | 12/1998 |
| WO | WO 00/06728 | 2/2000 |

OTHER PUBLICATIONS

Bertin et al., Human CARD4 Protein Is A Novel CED–4/Apaf–1 Cell Death Family Member . . . : J. of Biol. Chem. 274:12955–12958, 1999.
Inohara et al., "NOD1, an Apaf–1–like Activator of Caspase–9 and Nuclear Factor kB" J. of Biol. Chem. 274:14560–14567, 1999.
Marra et al., EMBL Accession No. AA620157, Sep. 12, 1996.
Baker et al., "Transducers of life and death: TNF receptor superfamily and associated proteins" Oncogene 12:1–9, 1996.
Chinnaiyan et al., "The cell–death machine" Current Biology 6:555–562, 1996.
Duan et al., "RAIDD is a new death adaptor molecule" Nature 385:86–89, 1997.
Epstein, F., "Nuclear factor–kB–A pivotal transcription factor in chronic inflammatory diseases" The New England J. of Medicine 336:1066–1071, 1997.
Hofman et al., "The CARD domain: a new apoptotic signalling motif" TIBS 22:155–156, 1997.
Hu et al., "Bcl–$X^L$ interacts with Apaf–1 and inhibits Apaf–1–dependent caspase–9 activation" Proc. Nat'l. Acad. Sci. USA 95:4386–4391, 1998.
Humke et al., "ICEBERG: A Novel Inhibitor of Interleukin–1β Generation" Cell 103:99–111, Sep. 29, 2000.
Inohara et al., "RICK, a novel protein kinase containing a caspase recruitment domain, interacts with . . . " J. of Biol. Chem. 273(20):12296–12300, 1998.
Li et al., "Cytochrome c and dATP–dependent formation of Apaf–1/caspase–9 complex initiates and apoptotic protease cascade" Cell 91:479–489, 1997.
Masumoto et al., "ASC, a Novel 22–kDa Protein, Aggregates During Apoptosis of . . . " J. of Biol. Chem. 274(48):33835–33838, 1999.
McCarthy et al., "RIP2 is a novel NF–kB–activating and cell death–inducing kinase" J. of Biol. Chem. 273(27):16968–16975, 1998.
Miura et al., "Induction of apoptosis in fibroblasts by IL–1β–converting enzyme, a mammalian homolog . . . " Cell 75:653–660, 1993.
Navab et al., "Pathogenesis of Atherosclerosis" American J. of Cardiology 76:18c–23c, 1995.
Reed, J., "Cytochrome c: Can't live with it–Can't live without it" Cell 91:559–562, 1997.
Wallach, D., "Cell death induction by TNF: a matter of self control" TIBS 22:107–109, 1997.
Yan et al., "mE10, a novel caspase recruitment domain–containing proapoptotic molecule" J. of Bio. Chem. 274(15)10287–10292, 1999.
GenBank Accession No. AA160647, Hillier et al., Dec. 1996.
GenBank Accession No. AA160649, Hillier et al., Dec. 1996.
GenBank Accession No. AA278825, Strausberg, Aug. 15, 1997.
GenBank Accession No. AA302352, Kerlavage, Apr. 18, 1997.
GenBank Accession No. AA528254, Strausberg, Aug. 5, 1997.
GenBank Accession No. AA573948, Strausberg, Sep. 12, 1997.
GenBank Accession No. AA582937, Strausberg, Sep. 26, 1997.
GenBank Accession No. AA723533, Hillier et al., Jan. 1998.
GenBank Accession No. AB023416, Masumoto et al., Dec. 1, 1999.

(List continued on next page.)

Primary Examiner—Sean McGarry
(74) Attorney, Agent, or Firm—Millennium Pharmaceuticals, Inc.

(57) ABSTRACT

The invention relates to CARD-3, a mediator of apoptosis. CARD-3 contains a CARD domain and a serine/threonine kinase domain. CARD-3 nucleic acids and polypeptides are useful in mediating apoptosis and in the identification of compounds which modulate apoptosis.

50 Claims, 10 Drawing Sheets

OTHER PUBLICATIONS

GenBank Accession No. AI148558, Strausberg, Oct. 28, 1998.
GenBank Accession No. AI262374, Strausberg, Nov. 13, 1998.
GenBank Accession No. AI346818, Strausberg, Feb. 2, 1999.
GenBank Accession No. AI570067, Strausberg, May 14, 19999.
GenBank Accession No. AI587178, Strausberg, May 14, 1999.
GenBank Accession No. AI821342, Strausberg, Jul. 9, 1999.
GenBank Accession No. AW192194, Strausberg, Nov. 29, 1999.
GenBank Accession No. AW196663, Strausberg, Nov. 29, 1999.
GenBank Accession No. R84288, Wilson, Aug. 14, 1995.

Met Asn Gly Glu Ala Ile Cys Ser Ala Leu Pro Thr Ile Pro Tyr His Lys Leu Ala Asp     20
Leu Arg Tyr Leu Ser Arg Gly Ala Leu Pro Thr Val Ser Gly Thr Val Ser Ala Asp Trp     40
Arg Val Gln Val Ala Val Lys His Leu His Ile Thr His Lys His Asp Ser Glu Arg         60
Lys Asp Val Leu Arg Glu Leu Ala Phe Leu Leu His Ile Ala Arg Phe Ser Ile Leu Pro     80
Ile Leu Gly Ile Cys Asn Glu Pro Glu Leu Gly Leu Val Thr Glu Tyr Met Pro Asn        100
Gly Ser Leu Asn Glu Leu Leu His Arg Lys Thr Glu Tyr Pro Asp Val Ala Trp Pro Leu    120
Arg Phe Arg Ile Leu His Glu Ile Ala Leu Gly Val Asn Tyr Leu His Asn Met Thr Pro    140
Pro Leu Leu His His Asp Leu Lys Thr Gln Asn Ile Leu Leu Asp Asn Glu Phe His Val    160
Lys Ile Ala Asp Phe Gly Leu Ser Lys Trp Arg Met Met Ser Leu Ser Gln Ser Arg Ser    180
Ser Lys Ser Ala Pro Glu Gly Gly Thr Ile Ile Tyr Met Pro Pro Glu Asn Tyr Glu Pro    200
Gly Gln Lys Ser Arg Ala Ser Ile Lys His Asp Ile Tyr Ser Tyr Ala Val Ile Thr Trp    220
Glu Val Leu Ser Arg Lys Gln Pro Phe Glu Asp Val Thr Asn Pro Leu Gln Ile Met Tyr    240
Ser Val Ser Gln Gly His Arg Pro Val Ile Asn Glu Glu Ser Leu Pro Tyr Asp Ile Pro    260
His Arg Ala Arg Met Ile Ser Leu Ile Glu Ser Gly Trp Ala Gln Asn Pro Asp Glu Arg    280
Pro Ser Phe Leu Lys Cys Leu Ile Glu Leu Glu Pro Val Leu Arg Thr Phe Glu Glu Ile    300
Thr Phe Leu Glu Ala Val Ile Gln Leu Lys Lys Thr Lys Leu Gln Ser Val Ser Ser Ala    320
Ile His Leu Cys Asp Lys Lys Lys Met Glu Leu Ser Leu Asn Ile Pro Val Asn His Gly    340
Pro Gln Glu Glu Ser Cys Gly Ser Ser Gln Leu His Glu Asn Ser Gly Ser Pro Glu Thr    360
Ser Arg Ser Leu Pro Ala Pro Gln Asp Asn Asp Phe Leu Ser Arg Lys Ala Gln Asp Cys    380
Tyr Phe Met Lys Leu His His Cys Pro Gly Asn His Trp Ser Thr Ser Thr Ile Ser Gly    400
Ser Gln Arg Ala Ala Phe Cys Asp His Lys Thr Thr Pro Cys Ser Ser Ala Ile Ile Asn    420
Pro Leu Ser Thr Ala Gly Asn Ser Glu Arg Leu Gln Pro Gly Ile Ala Gln Gln Trp Ile    440
Gln Ser Lys Arg Glu Asp Ile Val Asn Gln Met Thr Glu Ala Cys Leu Asn Gln Ser Leu    460
Asp Ala Leu Leu Ser Arg Asp Leu Ile Met Lys Glu Asp Tyr Glu Leu Val Ser Thr Lys    480
Pro Thr Arg Thr Ser Lys Val Arg Gln Leu Leu Asp Thr Thr Asp Ile Gln Gly Glu Glu    500
Phe Ala Lys Val Ile Val Gln Lys Leu Lys Asp Asn Lys Gln Met Gly Leu Gln Pro Tyr    520
Pro Glu Ile Leu Val Val Ser Arg Ser Pro Ser Leu Asn Leu Leu Gln Asn Lys Ser Met    540

(SEQ ID NO:1)

```
CCACGCGGTCCGGTCAGCTCTGGTTCGGAGAAGCAGCGGCTGGCGTGGCCATCCGGGGAATGGGC
GCCCTCGTGACCTAGTGTTGCGGGCAAAAAGGGTCTTGCCGGCCTCGTCGTGCAGGGCGTAT
CTGGGCGCCTGAGCGCGGGCGGTGGAGCCTTGGAGCCCGCGCAGCAGGGCACACCCGAACCG
GCTGAGCGCCCGGGACCATGAACGGGGAGCCGCCATCTGCAGGCCCTCTGGCACTGTCGTCCGCCCACG
CAAACTCGCCGACCTGCGCTACCTGAGCCGCGTGAAGCACCTGCACATCCACACTCCGCTGCTGACAGTGAA
CAGACTGGCGCGTCCAGGTGGCCGTGAAGCTGAAATTTTACACAAAGCTAGATTTAGTTACATTCTTCCAAT
AGAAAGGATGTCTTAAGAGAAGCTGAATTTTTGGGAATTGAATATCCTGATGTTGCTTGCCATTGAGATTTCGCATC
TTTGGAATTTGCAATGAACTCCTACATAGAGAAAACTGAATATCCTGATGTTGCTTGCCATTGAGATTTCGCATC
TAAATGAACTCCTACATAGAGAAAACTGAATATCCTGATGTTGCTTGCCATTGAGATTTCGCATC
CTGCATGAAATTGCCCTTGGTGTAAATTACCTGCACAATATGACTCCTCCTTTACTTCATCATGA
CTTGAAGACTCAGAATATCTTATTGGACAATGAATTTCATGTTAAGATTGCAGATTTTGGTTTAT
CAAAGTGGCGCATGATGTCCCTCTCACAGTCACGAAGTAGCAAATCTGCACCAGAAGGAGGACA
ATTATTCTATATGCCACCTGAAAACTATGAACCTGGAAGTGTTATCCAGAAAACAGCCTTTTGAAGATGTCA
TATATATAGCTATGCAGTTATCAGTGTATAGTGTGTCACAAGGACATCGACCTGTTAATGAAGAAAGT
CCAATCCTTTGCAGATATATACCTCACCGAGCGTATGATCTCTAATAGAAAGTGGATGGCACAAAA
TTGCCAATGATGAAAGACCATCTTCTTAAAATGTTTAATAGAACTGAACCAGTTTTGAGAACATTTG
TCCAGATGAAAGATAACTTTCTTGAAGCTGTTATTCAGCTAAAGAAAACAAAGTTACAGAGTGTTCAAGT
AAGAGATAACTTTCACCTATGTGACAAGAAGAAATGGAATTATCTGAACATACCTGTAAATCATGGTCC
GCCATTCACCTATGTGACAAGAAGAAATGGAATTATCTGAACATACCTGTAAATCATGGTCC
ACAAGAGAATCATGTGGATCCTCTCAGCTCTCCATGAAAATAGTGGTTCTCCTGAAACTTCAAGGT
CCCTGCCAGCTCCTCAAGACACAATGATTTTTATCTAGAAAAGCTCAAGACTGTGTTATTTTATGAAG
CTGCATCACTGTCCTGGAAATCACAGTGGGATAGCAATTTCTGGATTCTCAAAGGGCTGCATT
CTGTGATCACAAGACCATTCCATGCTCTTCAGCAGTGGTTCAGGAGCAAAAGGAAGACATTGTGAAC
CAGAACGTCTGGAGCCTGGCCTGTATAGCCAGGAGTGGATCCAGAGCAAAAGGAAGACATTGTGAAC
CAAATGACAGAAGCCTGCTGCCTTAACCAGTGTTAGTACCAAGCCTACAAAGTCAGAGGACTTGATCATGAA
AGAGGACTATGAACTTGTTAGTACCAAGCCTACAAAGTTATAGTACAAAAATTGAAAGATAACAACAA
CTACTGACATCCAAGGAGAAGAATTGCCAAAGTTATAGTACAAAAATTGAAAGATAACAACAA
ATGGTCTTCAGCTTACCCGAAATACTTGTGGTTTCTAGATCACCATCTTTAAATTTACTTCA
AATAAAGCATGTAAGTGACTGTTTTCAAGAAGAAATGTGTTTCATAAAGGATATTTATAAA
AAAAAAAAAAAAAAAAAAAAAAAAAAAAAAAAAAAAAAAAAA (SEQ ID NO:2)
```

```
Ser Asp Leu Leu Lys Asn Asp Tyr Phe Ser Ala Glu Asp Ala Glu Ile Val Cys Ala Cys      20
Pro Thr Gln Pro Asp Lys Val Arg Leu Lys Leu Asp Leu Ala Gln Ala Tyr Lys Gly Glu      40
Val Ser Glu Phe Phe Leu Tyr Leu Gly Phe Ser Pro Ser Leu Leu Arg Leu Asp Tyr Val Val  60
Pro Trp Leu Glu Ile Gly Phe Ser Arg Tyr Thr Gln Gln Gln His His Leu Gly Ile Val Val  80
Asn Thr Asp Pro Val Ser Arg Tyr Ala Gln Lys Glu Glu Glu Ile Leu Gly Arg Asp Ser     100
Lys Phe Val Leu Cys Tyr Ala Leu Val Gly Phe Ser Asn Glu Ser Leu Asn Ser Leu Ala    120
Thr Ile Met Glu Leu Asp His Thr Thr Gly Ile Leu Asn Gln Gly Leu Thr Ile Phe Ile Trp 140
Cys Leu Leu Gly Trp Ala Ser Pro Cys Cys Tyr Ser Gly Cys Arg Ala Ser Gly Pro Gln    160
Val Met Leu Gly Trp Ala Ser Pro Ala Xaa Val Lys Phe Phe Thr Phe Ala Xaa Ala Ala   180
Ala Arg Leu Asp Ala                                                                   200
```
(SEQ ID NO:3)

FIG. 3

```
CGTCCGACTTGCTGAAGAATGACTACTTCTCGGCCGAAGATGCGGAGATTGTGTGTGCCTGCCCC
ACCCAGCCTGACAAGGTCCGCAAAATTCTGGACCTGGTACAGAGCAAGGGCGAGGAGGTGTCCGA
GTTCTTCCTCTACTTGCTCCCAGCAACTCGGCAGCAACTCGTGGACCTCAGGCCTTGGACCCAGTGAGC
AGATCGGCTTCTCTCCCCTGCTCACTCAGAGCAGCCCGTGACTCAAGTTCGTGTGTATGCCCA
AGTATACCCAGCAGCTGCGACACCATCTGGGCCGTGACTCCAAGTTCGTGTGTATGCCCA
GAAGGAGGAGCTGCTGAGGAGATCTACATGGACACACCATCATGGACCATCATGGCTTCAGCA
ATGAGAGCCTGGGCAGCCTGAACAGCAGCCATCTGCCTGGCTGGTGGGGCAGCCATCCTCAAT
GAGCAGGGTGAGACATCTTCATCTGGGTGATGCTGGGGCAAGTCCATGCTGCTACAGCGG
CTGCAGAGCCTCTGCAGCCCCGGCCACAGCCCCGGCTAGAGCCAGGGTCAAATTCTTCTTCACTTTCGCTG
NCGCATGTTCAGCTGCTTAAGGAAAGTGCAGGTGTGTCTGA
```
(SEQ ID NO:4)

FIG. 4

```
  1 mgagatgram dgprllllll lgvslggake acptglyths gecckacnlg egvaqpcgan
 61 qtvcepclds vtfsdvvsat epckpctecv glqsmsapcv eaddavcrca ygyyqdettg
121 rceacrvcea gsglvfscqd kqntvceecp dgtysdeanh vdpclpctvc edterqlrec
181 trwadaecee ipgrwitrst ppegsdstap stqepeappe qdliastvag vvttvmgssq
241 pvvtrgttdn lipvycsila avvvglvayi afkrwnsckq nkqgansrpv nqtpppegek
301 lhsdsgisvd sqslhdqqph tqtasgqalk gdgglysslp pakreevekl lngsagdtwr
361 hlagelgyqp ehidsfthea cpvrallasw atqdsatlda llaalrriqr adlveslcse
421 statspv
```

FIGURE 13

```
  1 mrragaacsa mdrlrlllll ilgvssggak etcstglyth sgecckacnl gegvaqpcga
 61 nqtvcepcld nvtfsdvvsa tepckpctec lglqsmsapc veaddavcrc aygyyqdeet
121 ghceacsvce vgsglvfscq dkqntvceec pegtysdean hvdpclpctv cedterqlre
181 ctpwadaece eipgrwiprs tppegsdsta pstqepevpp eqdlvpstva dmvttvmgss
241 qpvvtrgttd nlipvycsil aavvglvay iafkrwnsck qnkqgansrp vnqtpppege
301 klhsdsgisv dsqslhdqqt htqtasgqal kgdgnlyssl pltkreevek llngdtwrhl
361 agelgyqpeh idsftheacp vrallaswga qdsatldall aalrrigrad iveslcsest
421 atspv
```

FIGURE 14

SEQUENCE LISTING

```
<160> NUMBER OF SEQ ID NOS: 14

<210> SEQ ID NO 1
<211> LENGTH: 540
<212> TYPE: PRT
<213> ORGANISM: Homo sapiens

<400> SEQUENCE: 1

Met Asn Gly Glu Ala Ile Cys Ser Ala Leu Pro Thr Ile Pro Tyr His
 1               5                  10                  15

Lys Leu Ala Asp Leu Arg Tyr Leu Ser Arg Gly Ala Ser Gly Thr Val
             20                  25                  30

Ser Ser Ala Arg His Ala Asp Trp Arg Val Gln Val Ala Val Lys His
         35                  40                  45

Leu His Ile His Thr Pro Leu Leu Asp Ser Glu Arg Lys Asp Val Leu
     50                  55                  60
```

-continued

```
Arg Glu Ala Glu Ile Leu His Lys Ala Arg Phe Ser Tyr Ile Leu Pro
 65                  70                  75                  80

Ile Leu Gly Ile Cys Asn Glu Pro Gly Phe Leu Gly Ile Val Thr Glu
                 85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
        275                 280                 285

Glu Leu Glu Pro Val Leu Arg Thr Phe Glu Glu Ile Thr Phe Leu Glu
    290                 295                 300

Ala Val Ile Gln Leu Lys Lys Thr Lys Leu Gln Ser Val Ser Ser Ala
305                 310                 315                 320

Ile His Leu Cys Asp Lys Lys Met Glu Leu Ser Leu Asn Ile Pro
                325                 330                 335

Val Asn His Gly Pro Gln Glu Glu Ser Cys Gly Ser Ser Gln Leu His
            340                 345                 350

Glu Asn Ser Gly Ser Pro Glu Thr Ser Arg Ser Leu Pro Ala Pro Gln
        355                 360                 365

Asp Asn Asp Phe Leu Ser Arg Lys Ala Gln Asp Cys Tyr Phe Met Lys
    370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Ile Pro Cys Ser Ser
                405                 410                 415

Ala Ile Ile Asn Pro Leu Ser Thr Ala Gly Asn Ser Glu Arg Leu Gln
            420                 425                 430

Pro Gly Ile Ala Gln Gln Trp Ile Gln Ser Lys Arg Glu Asp Ile Val
        435                 440                 445

Asn Gln Met Thr Glu Ala Cys Leu Asn Gln Ser Leu Asp Ala Leu Leu
    450                 455                 460

Ser Arg Asp Leu Ile Met Lys Glu Asp Tyr Glu Leu Val Ser Thr Lys
465                 470                 475                 480
```

```
Pro Thr Arg Thr Ser Lys Val Arg Gln Leu Leu Asp Thr Thr Asp Ile
            485                 490                 495

Gln Gly Glu Glu Phe Ala Lys Val Ile Val Gln Lys Leu Lys Asp Asn
        500                 505                 510

Lys Gln Met Gly Leu Gln Pro Tyr Pro Glu Ile Leu Val Val Ser Arg
    515                 520                 525

Ser Pro Ser Leu Asn Leu Leu Gln Asn Lys Ser Met
530                 535                 540

<210> SEQ ID NO 2
<211> LENGTH: 1931
<212> TYPE: DNA
<213> ORGANISM: Homo sapiens

<400> SEQUENCE: 2
```

| | | | | | |
|---|---|---|---|---|---|
| ccacgcgtcc | ggtcagctct | ggttcggaga | agcagcggct | ggcgtgggcc | atccggggaa | 60 |
| tgggcgccct | cgtgacctag | tgttgcgggg | caaaaagggt | cttgccggcc | tcgctcgtgc | 120 |
| agggcgtat | ctgggcgcct | gagcgcggcg | tgggagcctt | gggagccgcc | gcagcagggg | 180 |
| gcacacccgg | aaccggcctg | agcgcccggg | accatgaacg | gggaggccat | ctgcagcgcc | 240 |
| ctgcccacca | ttccctacca | caaactcgcc | gacctgcgct | acctgagccg | cggcgcctct | 300 |
| ggcactgtgt | cgtccgcccg | ccacgcagac | tggcgcgtcc | aggtggccgt | gaagcacctg | 360 |
| cacatccaca | ctccgctgct | cgacagtgaa | agaaaggatg | tcttaagaga | agctgaaatt | 420 |
| ttacacaaag | ctagatttag | ttacattctt | ccaattttgg | gaatttgcaa | tgagcctgaa | 480 |
| tttttgggaa | tagttactga | atacatgcca | aatggatcat | taaatgaact | cctacatagg | 540 |
| aaaactgaat | atcctgatgt | tgcttggcca | ttgagatttc | gcatcctgca | tgaaattgcc | 600 |
| cttggtgtaa | attacctgca | caatatgact | cctcctttac | ttcatcatga | cttgaagact | 660 |
| cagaatatct | tattggacaa | tgaatttcat | gttaagattg | cagattttgg | tttatcaaag | 720 |
| tggcgcatga | tgtccctctc | acagtcacga | agtagcaaat | ctgcaccaga | aggagggaca | 780 |
| attatctata | tgccacctga | aaactatgaa | cctggacaaa | aatcaaggcc | agtatcaag | 840 |
| cacgatatat | atagctatgc | agttatcaca | tgggaagtgt | tatccagaaa | acagccttt | 900 |
| gaagatgtca | ccaatccttt | gcagataatg | tatagtgtgt | cacaaggaca | tcgacctgtt | 960 |
| attaatgaag | aaagtttgcc | atatgatata | cctcaccgag | cacgtatgat | ctctctaata | 1020 |
| gaaagtggat | gggcacaaaa | tccagatgaa | agaccatctt | tcttaaaatg | tttaatagaa | 1080 |
| cttgaaccag | ttttgagaac | atttgaagag | ataacttttc | ttgaagctgt | tattcagcta | 1140 |
| aagaaaacaa | agttacagag | tgtttcaagt | gccattcacc | tatgtgacaa | gaagaaaatg | 1200 |
| gaattatctc | tgaacatacc | tgtaaatcat | ggtccacaag | aggaatcatg | tggatcctct | 1260 |
| cagctccatg | aaaatagtgg | ttctcctgaa | acttcaaggt | ccctgccagc | tcctcaagac | 1320 |
| aatgattttt | tatctagaaa | agctcaagac | tgttatttta | tgaagctgca | tcactgtcct | 1380 |
| ggaaatcaca | gttgggatag | caccatttct | ggatctcaaa | gggctgcatt | ctgtgatcac | 1440 |
| aagaccattc | catgctcttc | agcaataata | aatccactct | caactgcagg | aaactcagaa | 1500 |
| cgtctgcagc | ctggtatagc | ccagcagtgg | atccagagca | aagggaaga | cattgtgaac | 1560 |
| caaatgacag | aagcctgcct | taaccagtcg | ctagatgccc | ttctgtccag | ggacttgatc | 1620 |
| atgaaagagg | actatgaact | tgttagtacc | aagcctacaa | ggacctcaaa | agtcagacaa | 1680 |
| ttactagaca | ctactgacat | ccaaggagaa | gaatttgcca | aagttatagt | acaaaaattg | 1740 |
| aaagataaca | aacaaatggg | tcttcagcct | tacccggaaa | tacttgtggt | ttctagatca | 1800 |

```
ccatctttaa atttacttca aaataaaagc atgtaagtga ctgttttttca agaagaaatg    1860 tgtttcataa aaggatattt ataaaaaaaa aaaaaaaaaa aaaaaaaaaa aaaaaaaaaa    1920
aaaaaaaaaa a                                                         1931
```

<210> SEQ ID NO 3
<211> LENGTH: 200
<212> TYPE: PRT
<213> ORGANISM: Homo sapiens
<220> FEATURE:
<221> NAME/KEY: VARIANT
<222> LOCATION: (1)...(200)
<223> OTHER INFORMATION: Xaa = Any Amino Acid

<400> SEQUENCE: 3

```
Ser Asp Leu Leu Lys Asn Asp Tyr Phe Ser Ala Glu Asp Ala Glu Ile
 1               5                  10                  15

Val Cys Ala Cys Pro Thr Gln Pro Asp Lys Val Arg Lys Ile Leu Asp
            20                  25                  30

Leu Val Gln Ser Lys Gly Glu Glu Val Ser Glu Phe Phe Leu Tyr Leu
        35                  40                  45

Leu Gln Gln Leu Ala Asp Ala Tyr Val Asp Leu Arg Pro Trp Leu Leu
    50                  55                  60

Glu Ile Gly Phe Xaa Pro Ser Leu Leu Thr Gln Ser Lys Val Val Val
65                  70                  75                  80

Asn Thr Asp Pro Val Ser Arg Tyr Thr Gln Gln Leu Arg His His Leu
                85                  90                  95

Gly Arg Asp Ser Lys Phe Val Leu Cys Tyr Ala Gln Lys Glu Glu Leu
            100                 105                 110

Leu Leu Glu Glu Ile Tyr Met Asp Thr Ile Met Glu Leu Val Gly Phe
        115                 120                 125

Ser Asn Glu Ser Leu Gly Ser Leu Asn Ser Leu Ala Cys Leu Leu Asp
    130                 135                 140

His Thr Thr Gly Ile Leu Asn Glu Gln Gly Glu Thr Ile Phe Ile Trp
145                 150                 155                 160

Val Met Leu Gly Trp Ala Ser Pro Cys Cys Tyr Ser Gly Cys Arg Ala
                165                 170                 175

Ser Gly Pro Gln Ala Arg Leu Asp Ala Xaa Val Lys Phe Phe Phe Thr
            180                 185                 190

Phe Ala Xaa Ala Cys Ser Ala Ala
        195                 200
```

<210> SEQ ID NO 4
<211> LENGTH: 626
<212> TYPE: DNA
<213> ORGANISM: Homo sapiens
<220> FEATURE:
<221> NAME/KEY: misc_feature
<222> LOCATION: (1)...(626)
<223> OTHER INFORMATION: n = A,T,C or G

<400> SEQUENCE: 4

```
cgtccgactt gctgaagaat gactacttct cggccgaaga tgcggagatt gtgtgtgcct      60
gccccaccca gcctgacaag gtccgcaaaa ttctggacct ggtacagagc aagggcgagg     120
aggtgtccga gttcttcctc tacttgctcc agcaactcgc agatgcctac gtggacctca     180
ggccttggct gctggagatc ggcttctccc cttccctgct cactcagagc aaagtcgtgg     240
tcaacactga cccagtgagc aggtataccc agcagctgcg acaccatctg ggccgtgact     300
```

```
ccaagttcgt gctgtgctat gcccagaagg aggagctgct gctggaggag atctacatgg      360
acaccatcat ggagctggtt ggcttcagca atgagagcct gggcagcctg aacagcctgg      420
cctgcctact ggaccacacc accggcatcc tcaatgagca gggtgagacc atcttcatct      480
gggtgatgct ggggtgggca agtccatgct gctacagcgg ctgcagagcc tctgggccac      540
aggcccggct agacgcangg gtcaaattct tcttcacttt cgctgncgca tgttcagctg      600
cttaaggaaa gtgcaggtgt gtctga                                          626

<210> SEQ ID NO 5
<211> LENGTH: 22
<212> TYPE: DNA
<213> ORGANISM: Artificial Sequence
<220> FEATURE:
<223> OTHER INFORMATION: Synthetically derived primer

<400> SEQUENCE: 5
ggatatggrg accactgtga tg                                               22

<210> SEQ ID NO 6
<211> LENGTH: 32
<212> TYPE: DNA
<213> ORGANISM: Artificial Sequence
<220> FEATURE:
<223> OTHER INFORMATION: Synthetically derived primer

<400> SEQUENCE: 6
ataagggccc tcatgtggca gtggactcgc tg                                    32

<210> SEQ ID NO 7
<211> LENGTH: 34
<212> TYPE: DNA
<213> ORGANISM: Artificial Sequence
<220> FEATURE:
<223> OTHER INFORMATION: Synthetically derived primer

<400> SEQUENCE: 7
ataagggccc rcagcgtcgc agggcggcta aaag                                  34

<210> SEQ ID NO 8
<211> LENGTH: 31
<212> TYPE: DNA
<213> ORGANISM: Artificial Sequence
<220> FEATURE:
<223> OTHER INFORMATION: Synthetically derived primer

<400> SEQUENCE: 8
ataagggccc tcaggcaccc cagctggcca g                                     31

<210> SEQ ID NO 9
<211> LENGTH: 32
<212> TYPE: DNA
<213> ORGANISM: Artificial Sequence
<220> FEATURE:
<223> OTHER INFORMATION: Synthetically derived primer

<400> SEQUENCE: 9
cggggtacca tgaagctgca tcactgtcct gg                                    32

<210> SEQ ID NO 10
<211> LENGTH: 54
<212> TYPE: DNA
<213> ORGANISM: Artificial Sequence
<220> FEATURE:
```

<223> OTHER INFORMATION: Synthetically derived primer

<400> SEQUENCE: 10
ttttcctttt gcggccgctt acatgctttt attttgaagt aaatttaaag atgg    54

<210> SEQ ID NO 11
<211> LENGTH: 71
<212> TYPE: DNA
<213> ORGANISM: Artificial Sequence
<220> FEATURE:
<223> OTHER INFORMATION: Synthetically derived primer

<400> SEQUENCE: 11
cggaattcac catggaacag aaattgatct ccgaagaaga cttgggtacc atgaacgggg    60
aggccatctg c    71

<210> SEQ ID NO 12
<211> LENGTH: 54
<212> TYPE: DNA
<213> ORGANISM: Artificial Sequence
<220> FEATURE:
<223> OTHER INFORMATION: Synthetically derived primer

<400> SEQUENCE: 12
ttttcctttt gcggccgctt acatgctttt attttgaagt aaatttaaag atgg    54

<210> SEQ ID NO 13
<211> LENGTH: 427
<212> TYPE: PRT
<213> ORGANISM: Homo sapiens

<400> SEQUENCE: 13

Met Gly Ala Gly Ala Thr Gly Arg Ala Met Asp Gly Pro Arg Leu Leu
 1               5                  10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
    65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
                100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
        130                 135                 140

Val Cys Glu Glu Cys Pro Asp Gly Thr Tyr Ser Asp Glu Ala Asn His
    145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
                180                 185                 190

Gly Arg Trp Ile Thr Arg Ser Thr Pro Pro Glu Gly Ser Asp Ser Thr
            195                 200                 205

-continued

```
Ala Pro Ser Thr Gln Glu Pro Glu Ala Pro Pro Glu Gln Asp Leu Ile
    210                 215                 220

Ala Ser Thr Val Ala Gly Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Gly Leu Val Ala Tyr Ile Ala Phe
            260                 265                 270

Lys Arg Trp Asn Ser Cys Lys Gln Asn Lys Gln Gly Ala Asn Ser Arg
                275                 280                 285

Pro Val Asn Gln Thr Pro Pro Glu Gly Glu Lys Leu His Ser Asp
    290                 295                 300

Ser Gly Ile Ser Val Asp Ser Gln Ser Leu His Asp Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
                340                 345                 350

Gly Ser Ala Gly Asp Thr Trp Arg His Leu Ala Gly Glu Leu Gly Tyr
                355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
                420                 425

<210> SEQ ID NO 14
<211> LENGTH: 425
<212> TYPE: PRT
<213> ORGANISM: Rattus rattus

<400> SEQUENCE: 14

Met Arg Arg Ala Gly Ala Ala Cys Ser Ala Met Asp Arg Leu Arg Leu
1               5                   10                  15

Leu Leu Leu Leu Ile Leu Gly Val Ser Ser Gly Gly Ala Lys Glu Thr
                20                  25                  30

Cys Ser Thr Gly Leu Tyr Thr His Ser Gly Glu Cys Cys Lys Ala Cys
            35                  40                  45

Asn Leu Gly Glu Gly Val Ala Gln Pro Cys Gly Ala Asn Gln Thr Val
    50                  55                  60

Cys Glu Pro Cys Leu Asp Asn Val Thr Phe Ser Asp Val Val Ser Ala
65                  70                  75                  80

Thr Glu Pro Cys Lys Pro Cys Thr Glu Cys Leu Gly Leu Gln Ser Met
                85                  90                  95

Ser Ala Pro Cys Val Glu Ala Asp Asp Ala Val Cys Arg Cys Ala Tyr
                100                 105                 110

Gly Tyr Tyr Gln Asp Glu Glu Thr Gly His Cys Glu Ala Cys Ser Val
            115                 120                 125

Cys Glu Val Gly Ser Gly Leu Val Phe Ser Cys Gln Asp Lys Gln Asn
    130                 135                 140

Thr Val Cys Glu Glu Cys Pro Glu Gly Thr Tyr Ser Asp Glu Ala Asn
145                 150                 155                 160
```

-continued

```
His Val Asp Pro Cys Leu Pro Cys Thr Val Cys Glu Asp Thr Glu Arg
            165             170             175

Gln Leu Arg Glu Cys Thr Pro Trp Ala Asp Ala Glu Cys Glu Glu Ile
            180             185             190

Pro Gly Arg Trp Ile Pro Arg Ser Thr Pro Pro Glu Gly Ser Asp Ser
            195             200             205

Thr Ala Pro Ser Thr Gln Glu Pro Glu Val Pro Pro Glu Gln Asp Leu
        210             215             220

Val Pro Ser Thr Val Ala Asp Met Val Thr Thr Val Met Gly Ser Ser
225             230             235             240

Gln Pro Val Val Thr Arg Gly Thr Thr Asp Asn Leu Ile Pro Val Tyr
            245             250             255

Cys Ser Ile Leu Ala Ala Val Val Gly Leu Val Ala Tyr Ile Ala
            260             265             270

Phe Lys Arg Trp Asn Ser Cys Lys Gln Asn Lys Gln Gly Ala Asn Ser
            275             280             285

Arg Pro Val Asn Gln Thr Pro Pro Glu Gly Glu Lys Leu His Ser
    290             295             300

Asp Ser Gly Ile Ser Val Asp Ser Gln Ser Leu His Asp Gln Gln Thr
305             310             315             320

His Thr Gln Thr Ala Ser Gly Gln Ala Leu Lys Gly Asp Gly Asn Leu
            325             330             335

Tyr Ser Ser Leu Pro Leu Thr Lys Arg Glu Glu Val Glu Lys Leu Leu
            340             345             350

Asn Gly Asp Thr Trp Arg His Leu Ala Gly Glu Leu Gly Tyr Gln Pro
            355             360             365

Glu His Ile Asp Ser Phe Thr His Glu Ala Cys Pro Val Arg Ala Leu
    370             375             380

Leu Ala Ser Trp Gly Ala Gln Asp Ser Ala Thr Leu Asp Ala Leu Leu
385             390             395             400

Ala Ala Leu Arg Arg Ile Gln Arg Ala Asp Ile Val Glu Ser Leu Cys
            405             410             415

Ser Glu Ser Thr Ala Thr Ser Pro Val
            420             425
```

MOLECULES OF THE CARD-RELATED PROTEIN FAMILY AND USES THEREOF

RELATED APPLICATION INFORMATION

This application is a continuation-in-part of application Ser. No. 09/099,041, filed Jun. 17, 1998, now U.S. Pat. No. 6,340,576, which is a continuation-in-part of application Ser. No. 09/019,942, filed Feb. 6, 1998, now U.S. Pat. No. 6,033,855.

BACKGROUND

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as C. elegans, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are cysteine protease having specificity for aspartate at the substrate cleavage site. These proteases are primarily responsible for the degradation of cellular proteins that lead to the morphological changes seen in cells undergoing apoptosis. For example, one of the caspases identified in humans was previously known as the interleukin-1β (IL-1β) converting enzyme (ICE), a cysteine protease responsible for the processing of pro-IL-1β to the active cytokine. Overexpression of ICE in Rat-1 fibroblasts induces apoptosis (Miura et al., Cell 75:653 [1993]).

Many caspases and proteins that interact with caspases possess domains of about 60 amino acids called a caspase recruitment domain (CARD). Hofmann et al. (TIBS 22:155 [1997]) and others have postulated that certain apoptotic proteins bind to each other via their CARDs and that different subtypes of CARDs may confer binding specificity, regulating the activity of various caspases, for example.

The functional significance of CARDs have been demonstrated in two recent publications. Duan et al. (Nature 385:86 [1997]) showed that deleting the CARD at the N-terminus of RAIDD, a newly identified protein involved in apoptosis, abolished the ability of RAIDD to bind to caspases. In addition, Li et al. (Cell 91:479 [1997]) showed that the N-terminal 97 amino acids of apoptotic protease activating factor-1 (Apaf-1) was sufficient to confer caspase-9-binding ability.

SUMMARY

The invention relates to the discovery of two genes, card-3 (cDNA in FIG. 2, SEQ ID NO:2) and card-4 (partial cDNA in FIG. 4, SEQ ID NO:4), which encode the CARD-containing proteins CARD-3 (FIG. 1, SEQ ID NO:1) and CARD-4 (partial sequence in FIG. 3, SEQ ID NO:3).

CARD-3 contains a kinase domain at amino acid positions 1–300, followed by a linker domain at positions 301–431 and a CARD at positions 432–540. In the CARD-4 partial amino acid sequence (FIG. 3, SEQ ID NO:3), a CARD is located at positions 3–72, counting the first Ser in the sequence as the first position. Like other proteins containing a CARD, CARD-3 and CARD-4 are expected to participate in the network of interactions that lead to caspase activation. Accordingly, the human card-3 and card-4 genes described herein may be useful in diagnostic and therapeutic applications directed to the regulation of cell growth and death such as the diagnosis of certain cancers, e.g., breast cancer and colorectal cancer. These genes and the proteins they encode can be used to screen for molecules which inhibit or enhance CARD-3 or CARD-4 activity. Moreover, agonist ligands which bind to the proteins encoded by these genes may be useful for the treatment of certain cancers.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, or abnormal activity of a caspase by administering a compound that modulates the expression of CARD-3 and/or CARD-4 (at the DNA, mRNA or protein level, e.g., by altering mRNA splicing) or by altering the activity of CARD-3 and/or CARD-4. Examples of such compounds include small molecules, antisense nucleic acid molecules, ribozymes, and polypeptides.

Certain disorders are associated with an increased number of surviving cells, which are produced and continue to survive or proliferate when apoptosis is inhibited. These disorders include cancer (particularly follicular lymphomas, carcinomas associated with mutations in p53, and hormone-dependent tumors such as breast cancer, prostate cancer, and ovarian cancer), autoimmune disorders (such as systemic lupus erythematosis, immune-mediated glomerulonephritis), and viral infections (such as those caused by herpesviruses, poxviruses, and adenoviruses).

Failure to remove autoimmune cells that arise during development or that develop as a result of somatic mutation during an immune response can result in autoimmune disease. One of the molecules that plays a critical role in regulating cell death in lymphocytes is the cell surface receptor for Fas.

Populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

The invention features isolated nucleic acid molecules (i.e., a nucleic acid molecule that is separated from the 5' and 3' coding sequences of other genes with which it is immediately contiguous in the naturally occurring genome of an organism, also referred to as a recombinant nucleic acid molecule) that encodes a CARD-3 or CARD-4 polypeptide. Within the invention are polypeptides having the sequence of SEQ ID NO:1 or SEQ ID NO:3, or encoded by nucleic acid molecules having the sequence shown in SEQ ID NO:2 or SEQ ID NO:4. However, the invention is not limited to nucleic acid molecules and polypeptides that are identical to those SEQ ID Nos 1–4. For example, the invention includes nucleic acid molecules which encode splice variants, allelic variants, mutant forms, and full-length forms of card-3 or card-4 as well as the proteins encoded by such nucleic acid molecules.

Also within the invention are nucleic acid molecules that hybridize under stringent conditions to a nucleic acid molecule having the sequence of SEQ ID NO:2 or SEQ ID NO:4. Such molecules include, for example, other mammalian homologues of card-3 or card-4. As described further below, molecules that are substantially identical to those of SEQ ID Nos 1–4 are also encompassed by the invention.

Accordingly, the invention relates to isolated nucleic acid molecules which encode CARD-3 or CARD-4 polypeptides or variants thereof. Such polypeptides or fragments thereof can include the amino acid sequence of SEQ ID NO:1, the amino acid sequence of SEQ ID NO:3, at least 15 contiguous amino acids of SEQ ID NO:1, at least 15 contiguous amino acids of SEQ ID NO:3, amino acids from about 1 to about 300 (e.g., amino acids 20 to 320) of SEQ ID NO:1 (kinase domain); amino acids from about 301 to about 341 (e.g., amino acids 281 to 361 or 321 to 341) of SEQ ID NO:1 (linker domain); amino acids from about 432 to about 540 (e.g., amino acids 412 to 560 or 452 to 520) of SEQ ID NO:1 (CARD domain), or amino acids from about 3 to about 72 (e.g., amino acids 1 to 92 or 23 to 52) of SEQ ID NO:3 (CARD domain).

In addition, the isolated nucleic acid molecules of the invention can include the nucleotide sequence of SEQ ID NO:2 or 4 (or the RNA variants thereof), a nucleotide sequence complementary to SEQ ID NO:2 or 4, or a nucleic acid fragment of any previous nucleic acid molecule of at least 15 nucleotides in length. The isolated nucleic acid molecules further include nucleic acid molecules which encode polypeptides that are at least 80% identical to SEQ ID NO:1, nucleic acid molecules which encode polypeptides that are at least 80% identical to SEQ ID NO:3, nucleic acid molecules which hybridize under stringent conditions to the nucleic acid molecule of SEQ ID NO:2, nucleic acid molecules which hybridize under stringent conditions to the nucleic acid molecule of SEQ ID NO:4, nucleic acid molecules which hybridize under stringent conditions to the cDNA sequence contained within ATCC Accession No. 203037.

The invention further relates to methods for detecting the presence of any nucleic acid molecule described above by contacting a sample (e.g., one containing mRNA molecules) suspected of containing the nucleic acid molecule with a nucleic acid probe which selectively hybridizes to the nucleic acid molecule and determining whether the nucleic acid probe binds to the nucleic acid molecule in the sample. A nucleic acid probe is a nucleic acid molecule or analog thereof which is capable of sequence specific binding to a target nucleic acid. Such probes can be labeled with a detectable label (e.g., a chromogenic converting enzyme such as horseradish peroxidase or a radioisotope).

The invention also features substantially pure CARD-3 and CARD-4 polypeptides and fragments thereof, each polypeptide or fragment having at least one functional domain of CARD-3 or CARD-4 (e.g., the kinase domain, linker domain, or CARD of CARD-3; or the CARD of CARD-4).

Thus, the invention relates to substantially pure polypeptides having the amino acid sequence of SEQ ID NO:1, having the amino acid sequence of SEQ ID NO:3, having at least 15 contiguous amino acids of SEQ ID NO:1, having at least 15 contiguous amino acids of SEQ ID NO:3, having amino acids from about 1 to about 300 of SEQ ID NO:1 (kinase domain), having amino acids from about 301 to about 341 of SEQ ID NO:1 (linker domain); having amino acids from about 432 to about 540 of SEQ ID NO:1 (card domain), or having amino acids from about 3 to about 72 of SEQ ID NO:3 (card domain). In addition, the invention features methods for producing the aforementioned substantially pure polypeptides of the invention by culturing a host cell (e.g., a bacterium) containing an aforementioned nucleic acid molecule which expresses the polypeptide.

This invention also features hybrid molecules comprising a polypeptide of the invention fused to a heterologous polypeptide (e.g., the CARD of CARD-3 fused to β-galactosidase).

The term "substantially pure" as used herein in reference to a given compound (e.g., a CARD-3 or CARD-4 polypeptide) means that the compound is substantially free from other compounds, such as those in cellular material, viral material, or culture medium, with which the compound may have been associated (e.g., in the course of production by recombinant DNA techniques or before purification from a natural biological source). When chemically synthesized, a compound of the invention is substantially pure when it is substantially free from the chemical compounds used in the process of its synthesis. Polypeptides or other compounds of interest are substantially free from other compounds when they are within preparations that are at least 60% by dry weight the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably at least 100 nucleotides (e.g., 150, 200, 250, or 300 nucleotides).

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (e.g., the Sequence Analysis Software Package of the Genetics Computer Group, University of Wisconsin Biotechnology Center, 1710 University Avenue, Madison, Wis. 53705 with the default parameters as specified therein.

The BLAST programs, provided as a service by the National Center for Biotechnology Information (Bethesda, Md.) are very useful for melting sequence comparisons. The programs are described in detail by Karlin et al. (Proc Natl Acad Sci USA 87:2264 [1990] and Proc Natl Acad Sci USA 90:5873 [1993]) and Altschul et al. (Nucl Acids Res 25:3389 [1997]).

The invention also features a host cell that includes an isolated nucleic acid molecule encoding CARD-3 or CARD-4 (either alone or in conjunction with a heterologous polypeptide, such as a detectable marker), or a nucleic acid vector that contains a sequence encoding CARD-3 or CARD-4 (again, with or without a heterologous polypeptide). The vector can be an expression vector, and can include a regulatory element.

An antibody that specifically binds a CARD-3 or CARD-4 polypeptide is also within the scope of the present invention and is useful, for example, to detect CARD-3 or CARD-4 in a biological sample, or to alter the activity of CARD-3 or CARD-4. For example, CARD-3 or CARD-4 can be detected in a biological sample by contacting the sample with an antibody that specifically binds CARD-3 or CARD-4 under conditions that allow the formation of a CARD-3- or CARD-4 antibody complex and detecting the complex, if present, as an indication of the presence of CARD-3 or CARD-4 in the sample. The use of an antibody in a treatment regime, where it can alter the activity of CARD-3 or CARD-4, is discussed further below.

Accordingly, the invention features methods for detecting the presence of an aforementioned polypeptide by contacting the sample suspected of containing the polypeptide with a compound (e.g., an antibody) which selectively binds to the polypeptide and determining whether the compound binds to the polypeptide in the sample.

An antibody of the invention can be a monoclonal, polyclonal, or engineered antibody that specifically binds CARD-3 or CARD-4 (as described more fully below). An antibody that "specifically binds" to a particular antigen, for example, a CARD-3 or CARD-4 polypeptide of the invention, will not substantially recognize or bind to other molecules in a sample, such as a biological sample, that includes CARD-3 or CARD-4. Thus, the invention also features methods for identifying a test compound (e.g., an antibody) which binds to a polypeptide of the invention by contacting the polypeptide with a test compound and determining whether the polypeptide binds to the test compound (e.g. by direct detection of the binding, detection of a competitor molecule which disrupts binding of the test compound to the polypeptide, and/or detection of binding using an assay for apoptosis activity).

Given that an object of the present invention is to alter the expression or activity of card-3 or card-4 in vivo, a pharmaceutical composition containing, for example, isolated nucleic acid molecules encoding CARD-3 or CARD-4 proteins (or fragments thereof), nucleic acid molecules that are antisense to card-3 or card-4 (i.e., that have a sequence that is the reverse and complement of a portion of the coding strands of card-3 or card-4 genes), CARD-3 or CARD-4 polypeptides, or antibodies, small molecules, or other compounds that specifically bind CARD-3 or CARD-4 polypeptides are also a feature of the invention.

The discovery and characterization of card-3 and card-4 and the polypeptides they encode makes it possible to determine whether a given disorder is associated with aberrant expression of card-3 or card-4 (meaning expression at the level of gene transcription or mRNA translation) or activity of CARD-3 or CARD-4. For example, one can diagnose a patient as having a disorder associated with aberrant expression of card-3 or card-4 by measuring card-3 or card-4 expression in a biological sample obtained from the patient. An increase or decrease in card-3 or card-4 expression in the biological sample, compared with card-3 or card-4 expression in a control sample (e.g., a sample of the same tissue collected from one or more healthy individuals) indicates that the patient has a disorder associated with aberrant expression of card-3 or card-4. Similarly, one can diagnose a patient as having a disorder associated with aberrant activity of CARD-3 or CARD-4 by measuring CARD-3 or CARD-4 activity in a biological sample obtained from the patient. An increase or decrease in CARD-3 or CARD-4 activity in the biological sample, compared with CARD-3 or CARD-4 activity in a control sample, indicates that the patient has a disorder associated with aberrant activity of CARD-3 or CARD-4. The techniques required to measure gene expression or polypeptide activity are well known to those of ordinary skill in the art.

Thus, the invention features (1) methods for diagnosing a patient as having a disorder associated with aberrant expression of card-3 or card-4 by measuring card-3 or card-4 expression in a biological sample obtained from the patient where increased or decreased card-3 or card-4 expression in the biological sample compared with card-3 or card-4 expression in a control sample indicates that the patient has a disorder associated with aberrant expression of card-3 or card-4; (2) methods for diagnosing a patient as having a disorder associated with expression of an isoform of CARD-3 or CARD-4 by isolating card-3 or card-4 mRNA or CARD-3 or CARD-4 polypeptide from the patient and determining the sequence of the mRNA or polypeptide where a difference in the sequence as compared to the nucleotide sequence of SEQ ID NO:2 or 4 or the polypeptide sequence of SEQ ID NO:1 or 3 indicates expression of an isoform of CARD-3 or CARD-4; and (3) methods for diagnosing a patient as having a disorder associated with aberrant activity of CARD-3 or CARD-4 by measuring CARD-3 or CARD-4 activity in a biological sample obtained from the patient where increased or decreased CARD-3 or CARD-4 activity in the biological sample compared with CARD-3 or CARD-4 activity in a control sample indicates that the patient has a disorder associated with aberrant activity of CARD-3 or CARD-4.

In addition to diagnostic methods, such as those described above, the present invention encompasses methods and compositions for typing, evaluating the prognosis of, and appropriate treatment for, disorders associated with inappropriate expression of card-3 or card-4 or inappropriate activity of CARD-3 or CARD-4. For example, the nucleic acid molecules of the invention can be used as probes to classify cells in terms of their level of card-3 or card-4 expression, or as primers for diagnostic PCR analysis in which mutations, allelic variations, and regulatory defects in the card-3 or card-4 gene can be detected. Similarly, those of ordinary skill in the art can use routine techniques to identify inappropriate activity of CARD-3 or CARD-4, which can be observed in a variety of forms. For example, inappropriate activity can take the form of strong binding to inappropriate caspases. Diagnostic kits for the practice of such methods are also provided.

The invention further encompasses transgenic animals that express card-3 or card-4 and recombinant "knock-out" animals that fail to express card-3 or card-4. These animals can serve as new and useful models of disorders in which card-3 or card-4 expression is abnormal.

The invention also features antagonists and agonists of CARD-3 or CARD-4 that can inhibit or enhance, respectively, one or more of the biological activities of CARD-3 or CARD-4. Suitable antagonists can include small molecules (i.e., molecules with a molecular weight below about 500), large molecules (i.e., molecules with a molecular weight above about 500), antibodies that specifically bind and "neutralize" CARD-3 or CARD-4 (as described below), and nucleic acid molecules that interfere with transcription or translation of card-3 or card-4 (e.g., antisense nucleic acid molecules and ribozymes). Agonists of CARD-3 or CARD-4 also include small and large molecules, and antibodies other than neutralizing antibodies.

Thus, the invention features (1) methods for modulating (e.g., decreasing or increasing) an activity (e.g., the ability to recruit caspases) of an aforementioned polypeptide of the invention by contacting a cell expressing the polypeptide with a compound which binds to the polypeptide in a sufficient concentration to modulate the activity of the polypeptide; and (2) methods of identifying a compound that modulates the activity (e.g., decrease or increase) of an aforementioned polypeptide having a CARD of CARD-3 or a CARD of CARD-4 by contacting the polypeptide with a test compound (e.g., polypeptides, ribonucleic acids, small molecules, ribozymes, antisense oligonucleotides, and deoxyribonucleic acids) and detecting and comparing the level of activity of the polypeptide in the presence or absence of the test compound.

The invention also features molecules that can increase or decrease the expression of card-3 or card-4 (e.g., by altering transcription or translation). Small molecules (as defined above), large molecules (as defined above), and nucleic acid molecules (e.g., antisense and ribozyme molecules) can be used to inhibit the expression of card-3 or card-4. Other types of nucleic acid molecules (e.g., molecules that bind to card-3 or card-4 negative transcriptional regulatory sequences) can be used to increase the expression of card-3 or card-4. Accordingly, the invention features methods for modulating apoptosis by modulating the expression or activity of a gene containing the sequence of an aforementioned nucleic acid of the invention encoding a CARD of CARD-3 or a CARD of CARD-4.

Compounds that modulate the expression of card-3 or card-4 in a cell can be identified by comparing the level of expression of card-3 or card-4 in the presence of a selected compound with the level of expression of card-3 or card-4 in the absence of that compound. A difference in the level of card-3 or card-4 expression indicating that the selected compound modulates the expression of card-3 or card-4 in the cell. A comparable test for compounds that modulate the activity of CARD-3 or CARD-4 can be carried out by comparing the level of CARD-3 or CARD-4 activity in the presence and absence of the compound. Accordingly, the invention features methods of identifying a compound that modulates the expression of a gene (e.g., a gene comprising the sequence of an aforementioned nucleic acid molecule of the invention) encoding a polypeptide having a CARD of CARD-3 or a CARD of CARD-4 by contacting the gene with a test compound (e.g., polypeptides, ribonucleic acids, small molecules, ribozymes, antisense oligonucleotide, and deoxyribonucleic acids) and detecting and comparing the level of expression of the gene in the presence and absence.

Patients who have a disorder mediated by abnormal CARD-3 or CARD-4 activity can be treated by administration of a compound that alters the expression of card-3 or card-4 or the activity of CARD-3 or CARD-4. When the objective is to decrease expression or activity, the compound administered can be a card-3 or card-4 antisense oligonucleotide or an anti-CARD-3 or anti-CARD-4 antibody, such as a neutralizing antibody, that specifically binds CARD-3 or CARD-4, respectively. Accordingly, the invention features methods for treating a patient having a disorder associated with the aberrant expression or activity any aforementioned polypeptide of the invention having a CARD of CARD-3 or a CARD of CARD-4 by administering a therapeutically effective amount of a compound (e.g., polypeptide, ribonucleic acid, small molecule, ribozyme, antisense oligonucleotide or deoxyribonucleic acid) that decreases or increases the expression or activity of the gene (e.g., a gene comprising the sequence of any nucleic acid molecule of the invention).

Additional information concerning CARD-3 and CARD-4 can be found in U.S. Ser. No. 09/099,041 (filed Jun. 17, 1998), now U.S. Pat. No. 6,340,576. U.S. Ser. No. 09/207,359 (filed Dec. 8, 1998), now U.S. Pat. No. 6,469, 140, U.S. Ser. No. 09/245,281 (filed Feb. 5, 1999), now U.S. Pat. No. 6,369,196, and U.S. Ser. No. 09/340,620 (filed Jun. 28, 1999), now U.S. Pat. No. 6,482,933, the contents of which are incorporated by reference in their entirety.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In addition, the materials, methods, and examples are illustrative only and are not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts the human CARD-3 amino acid sequence (SEQ ID NO:2).

FIG. 2 depicts the human card-3 cDNA sequence SEQ ID NO:2.

FIG. 3 depicts a partial CARD-4 amino acid sequence (SEQ ID NO:3).

FIG. 4 depicts a partial human card-4 cDNA sequence (SEQ ID NO:4).

FIG. 13 depicts the amino acid of human nerve growth factor receptor (p75; Genbank® Accession No. 69065 or GQHUN (SEQ ID NO:13).

FIG. 14 depicts the amino acid of rat nerve growth factor receptor (p75; Genbank® Accession No. 92530 or A26431 (SEQ ID NO:14).

DETAILED DESCRIPTION

Figure 5:
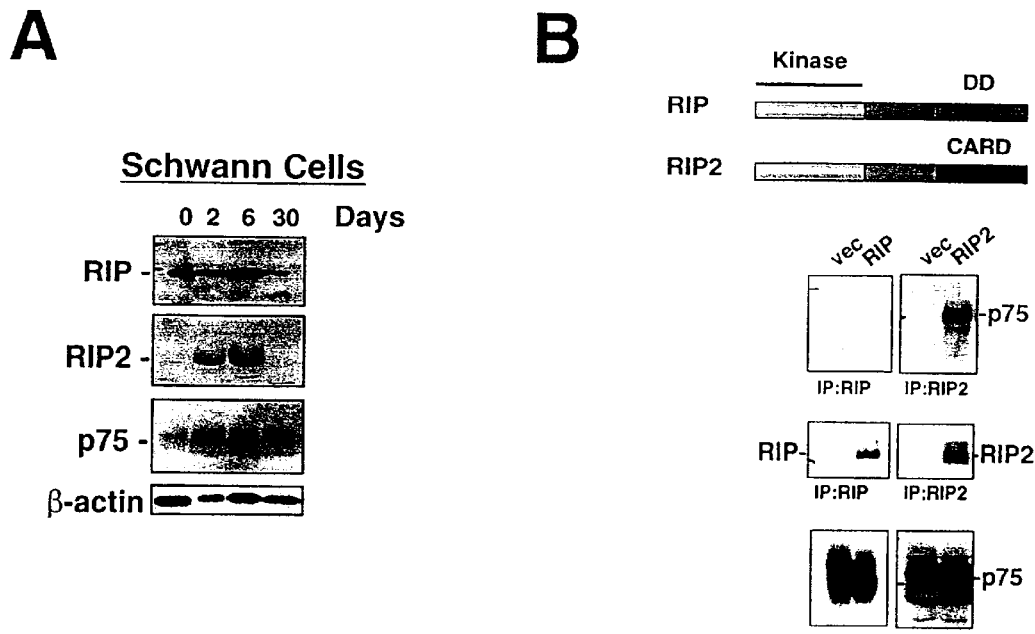
FIGS. 5A and 5B depict the results of a Western blot analysis demonstrating that CARD-3 binds to p75.

The invention relates to the discovery of two genes, card-3 (cDNA in FIG. 2, SEQ ID NO:2) and card-4 (partial cDNA in FIG. 4, SEQ ID NO:4), which encode the CARD-containing CARD-3 (FIG. 1, SEQ ID NO:1) and CARD-4 (partial sequence in FIG. 3, SEQ ID NO:3) proteins.

A plasmid containing a cDNA encoding human CARD-3 (pXE17A) was deposited with the American Type Culture Collection (ATCC), Manassas, Va. on May 14, 1998, and assigned Accession Number 203037. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. □112.

CARD-3 and CARD-4

CARD-3 contains a kinase domain at amino acid positions 1–300, followed by a linker domain at positions 301–431 and the CARD at positions 432–540. In the CARD-4 partial amino acid sequence (FIG. 3, SEQ ID NO:3), the CARD is at positions 3–72, counting the first Ser in FIG. 3 as position 1.

As described above, the nucleic acid molecules of the invention and the polypeptides they encode (e.g., CARD-3 or CARD-4 polypeptides or fragments thereof) can be used directly as diagnostic and therapeutic agents, or they can be used to generate antibodies or identify small molecules that, in turn, are clinically useful. In addition, card-3 or card-4 nucleic acid molecules are useful in genetic mapping, to identify the chromosomal location of card-3 or card-4, and as tissue-specific markers. Accordingly, expression vectors containing the nucleic acid molecules of the invention, cells transfected with these vectors, the polypeptides expressed, and antibodies generated, against either the entire polypeptide or an antigenic fragment thereof, are among the preferred embodiments. These embodiments and some of their clinical application are described further below.

The cDNA clone (SEQ ID NO:2) encoding the human CARD-3 and the partial cDNA clone (SEQ ID NO:4) encoding the partial human CARD-4 were isolated from a human cDNA library.

CARD-3 is also referred to as RIP2, RICK, and CARDIAK (McCarthy et al. (1998) *J. Biol. Chem.*273:16968; Naohiro et al. (1948) *J. Biol. Chem.*273:12296; and Thom et al. (1998) *Current Biol.* 8:885.

CARD-3 is a Mediator of p75

Neurotrophins such as NGF promote differentiation, growth and survival of diverse cell types in the nervous system (Lewin and Barde, 1996). In addition to promoting cell survival, neutrophins can cause cell death in certain cell types. Control of cell survival and death by members of the NGF neurotophin family is mediated by two transmembrane receptors, the Trk receptor tyrosine kinase and the p75 neurotrophin receptor (Chao, 1992). Survival responses caused by neurotrophins require activation of Trk receptor tyrosine kinases. In the presence of NGF, a ligand of the Trk receptor, the p75 receptor, participates in the formation of high affinity NGF binding sites and potentiates TrkA mediated signal transduction to promote survival under low concentrations of neurotrophins. By contrast, in the absence of Trk receptor, the p75 receptor is capable of initiating a cell death program in certain (Casaccia-Bonnefil et al. (1996) *Nature* 383:716; Frade et al. (1996) *Nature* 383:166; Bredesen et al. (1997) *TINS* 20:287; Bamji et al. (1998) *J. Cell. Biol.* 140:911). In addition, in the absence of Trk receptor signalling, activation of the p75 receptor is associated with increased production of ceramides and induction of NF-κB or JNK (Bothwell, M. (1996) *Science* 272:506; Carter et al. (1997) *Neuron* 18:187).

In addition to neuronal functions, neurotrophins also regulate Schwann cell viability and development. Following nerve injury or in the absence of axons, Schwann cells express high levels of p75 receptor (Lemke et al. (1988) *Development* 102:499; Taniuchi et al. (1998) *J. Neuroscience* 8:664), and studies suggest that Schwann cell migration is dependent upon p75 signaling (Anton et al. (1994) *Proc. Nat'l. Acad. Sci. USA* 91:2795; Bentley et al. (2000) *J. Neuroscience* 20:7706). Schwann cells also undergo apoptosis in response to NGF after axotomy or after trophic factor withdrawal. NGF-induced death is relatively absent in Schwann cells cultured from p75-/-mice (Soilu-Hanninen et al. (1999) *J. Neuroscience* 19:4828; Syroid et al. (2000) *J. Neuroscience* 20:5741). These results indicate that NGF signaling through the p75 receptor is critical in regulating both survival and apoptotic events, since the TrkA receptor is not expressed in Schwann cells.

The p75 neurotrophin receptor is a member of the TNF receptor superfamily which include the Fas (CD95) antigen, CD30, and CD40 (Smith et al. (1994) *Cell* 76:959). The intracellular region of several receptors in this family, including the p55 TNF receptor, Fas and the p75 neurotrophin, contains a sequence which has been designated the death domain (Feinstein et al. (1995) *TIBS* 20:342). This motif serves as a protein-protein docking site and is required for initiating TNF and Fas-dependent cytotoxicity. Activation of the TNF receptor members leads to the recruitment of adapter proteins including TNF receptor associated factors (TRAFs), and death domain-containing proteins TRADD (Hsu et al. (1995) *Cell* 81:495), FADD/MORT1 (Chinnaiyan et al. (1995) *Cell* 81:505) and RIP (Stranger et al. (1995) *Cell* 81:513; Hsu et al. (1996) *Immunity* 4:387). Members of the TNF receptor family use these adaptor proteins to mediate downstream effector functions, such as caspase activation, NF-κB and JNK activation.

The experiments described below illustrate how CARD-3 allows NGF to play a bi-functional role in determining cell survival and death decisions. In short, CARD-3 provides a switch for cell survival and cell death decisions mediated by p75 neutrophin receptor.

The following experimental techniques were employed in the experiments described below.

Plasmids and constructs: HA-tagged p75 deletions were generated by using polymerase chain reaction (PCR). A common 5'-PCR primer (5'-GGATATGGRGACCACTGTGATG-3'; SEQ ID NO:5) was used in conjunction with unique 3'-PCR primers for each particular deletion (D2, 5'ATAAGGGCCCTCATGTGGCAG TGGACTCGCTG-3'; SEQ ID NO:6; D3, 5'ATAAGGGCCCRCAGCGTCGCAGGGCGGCTAAA AG-3' SEQ ID NO:7; and D4, 5'ATAAGGGCCCTCAGGC ACCCCAGCTGGCCAG-3'; SEQ ID NO:8) and the pCDNA3 rat HA-tagged p75 cDNA was used as a template. All PCR product were cut with NarI and ApaI and ligated into a NanI and ApaI-digested pCDNA rat HA-tagged p75 sequence. All constructs were verified by DNA sequencing (Rockefeller University, New York, N.Y.).

The pC1 myc-tagged CARD-3 cDNA and myc-tagged CARD-3-DCARD cDNA constructs were kindly provided by Millennium Pharmaceuticals, Inc. The CARD-3-CARD was generated by PCR using a 5'-primer (5'CGGGGTACCATGAAGCTGCATCACTGTCCTGG-3'; SEQ ID NO:9) with a 3'-primer (5'TTTTCCTT TTGCG-GCCGCTTACATGCTTTTATTTTGAAGTAAA TTTAAA-GATGG3'; SEQ ID NO:10) and the pC1 CARD-3 cDNA as a template. The PCR product was digested with KpnI and NotI and ligated into a KpnI-, NotI digested CARD-3 construct with a KpnI site generated between the myc-epitope and CARD-3 sequence (5'CGGAATTCACCATG-GAACAGAAATTGATCTCCG AAGAAGACTTGGG-TACCATGAACGGGGAGGCCAT CTGC-3'; SEQ ID NO:11) and a 3'-primer (5'TTTTCCTT TTGCGGCCGCT-TACATGCTTTTATTTTGAAGTAA ATTTAAAGATGG-3'; SEQ ID NO:12) and using the pC1 CARD-3 as a template.

GSTp75 constructs-Rat p75 cDNA fragments encoding the entire cytoplasmic domain (amino acids 245–396) and the death domain (amino acids 302–396) were amplified by PCR and subloned into pGEX-4T1 vector (Pharmacia).

293 Cell Culture and Transfection: 293 cells were cultured in Dulbecco's modified Eagles' medium+10% fetal calf serum supplemented with penicillin-streptomycin (Life Technologies, Inc.) at 37° C. in 5% $CO_2$.

Isolation of Schwann Cells: Sciatic nerves were dissected from P2 rats, minced and incubated in Hanks Balanced solution containing 0.25% Tyrpsin (Sigma) and 0.25% collangase (Sigma) for 30 min. The cells are triturated, plated on ply-D-lysine coated 6 well plates cultured in Dulnbecco's modified Eagle's media containing 10% fetal calf serum and 2 μM forskolin (Sigma).

Luciferase assay: Schwann cells cultured for 4 days over 30 days were plated at 20,000 cells/well of a 12 well plate. Cells are transfected with 75 ng of NF-κB luciferase reporter containing two RB sites in pBIIX-luc cDNA (Gu et al. (1998) *FASEB J.* 12:1101), 75 ng of LacZ cDNA and 0.3 μg of cDNA using the Effectene Transfection Reagent kit, following the manufactures protocol (Qiagen). Following transfection, the cells were refed in DMEM+0.5% serum with or without 100 ng/ml of NGF for 24 hrs. Cells were lysed and analyzed for luciferase activity using the manufactures protocol (Promega). 293 cells were plated at 5×105 cells/well, transfected with a NF-κB reporter construct and either CARD-3, p75 or vector using the calcium phosphate method. After transfection, cells were treated with DMEM plus 1% FCS+/−100 ng/ml of NGF for an additional 24 hours. Cells were lysed and analyzed for luciferase activity. All transfections included a LacZ construct to normalize for transfection efficiency.

Immunoprecipitation: For myc-CARD-3 and p75 overexpression in 293 cells, approximately $1.5 \times 10^6$ cells in 10 cm tissue culture dishes were transfected with 10 μg of plasmid DNA (3 μg p75, 5 μg CARD-3) using the calcium phosphate method. Following a period of 36 hours after transfection, the cells were collected and aliquoted into microcentrifuge tubes at $2 \times 10^6$ cells/ml. NGF (100 ng/ml) was added to the tubes for 5 min. at room temperature, unless specified. The cells were then spun down and lysed in 1 ml of Nonidet P-40 lysis buffer (1% Nonidet P-40, 20 mM Tris, pH, 200 mM NaCl, 1 mM EDTA, 2 μg/ml aprotinin, 1 μg/ml leupeptin, and 25 μg/ml phenylmethylsulfonyl fluoride). Lysates (800 μg/ml) were incubated with α-myc (2 μg/ml; Santa Cruz Biotechnology) and Sepharose-Protein A (Sigma) or with α-myc Affinity gel (4 μg/ml; Santa Cruz Biotechnology). The matrix was washed and immune complexes were re-suspended in SDS-PAGE sample buffer and subjected to Western analysis. For the endogenous CARD-3 immunoprecipitation, Schwann cells were isolated the sciatic nerve taken from 120 pups and cultured as above for 6 days. The cultures were washed and incubated in serum free DMEM for 3 hrs before 100 ng/ml of NGF is added to the dish for t min. and then lysed in 1% Nonidet P-40 lysis buffer (see above). Lysates from Schwann cell (12 mg) were incubated with either anti-CARD-3 (anti-RICK) or normal rabbit IgG coupled to protein A Sepharose overnight. The matrix was washed and immune complexes were re-suspended in SDS-PAGE sample buffer and subjected to Western analysis (see below).

Western Analysis: Samples in SDS-Page sample buffer were resolved on a 10% SDS-polyacrylamide gel under reducing conditions. Proteins were transferred to PVDF membrane, blocked with 5% milk and incubated with a primary antibody (rabbit polyclonal a-p75 (a-9992) or rabbit polyclonal a-HA antibody (Immunotech) at room temperature. The membrane was washed with TBST and incubated with a α-mouse or α-rabbit IgG-horseradish peroxidase (Sigma) and then processed by ECL (Amersham) and exposed to x-ray film. For the endogenous expression of CARD-3, Schwann cells were isolated from sciatic nerves taken from 120 rat pups as described above. The cells were plated on poly-D-lysine coated wells. The cells were lysed in 1% NP-40 at day 0, 2, 6 or 30 days. Cell lysates (30 $\mu$g) were incubated in SDS-PAGE sample buffer and subjected to western analysis using anti-RICK (anti-CARD-3) antibody (StressGen).

TUNEL stain: After three days or over 30 days in culture, Schwann cells are plated onto a poly-D-lysine coated slides or chambers at 5,000 cells/chamber. After two serum free washes, the cells were incubated in DMEM and low serum (0.5–1% FBS) with or without 100 ng.ml of NGF for 24 hrs. The cells were fixed with 4% paraformaldyhe for 1 hour at room temperature and TUNEL labeling. The cells were also stained with DAPI (1:500) for 20 minutes and the cover slips were mounted using Vecta Shield. Cells were viewed at 40× on the Nikon scope, quantitated and represented as % nuclei positive for TUNEL stain.

GFP co-transfection: After three days or over 30 days in culture, Schwann cells were plated on poly-D-lysine coated chambers at 5,000 cells/chamber. Cells are transfected with 0.05 $\mu$g of GFP and 0.1 $\mu$g of DNCARD-3, CARD-3, or control vector. After 24 hrs in DMEM and 10% FBS, the cells were washed twice in serum-free media an incubated in low serum (0.5–1.0% FBS) with or without 100 ng/ml of NGF. GFP expressing cells were observed for apoptotic morphology 18–24 hrs later. The data is represented as the % of GFP cells exhibiting apoptotic morphology.

GST p75 assay: p75 GST fusion proteins were prepared and immobilized on glutathione-Sepharose 4B beads (Pharmacia) by following manufacture instruction. Full-length CARD-3 was in vitro-transdcribed/translated from pCl vector using TNT coupled reticulocyte system (Promega) with $^{35}$S-methionine (Amersham). The generated $^{35}$S-labeled CARD-3 protein was incubated with GST-p75 (245–396) or GST-p75 (302–396) BSA coated beads at 4° C. for several hours to overnight in TNE buffer (10 MM Tris (pH 8.0), 150 mM NaCl, 1 mM EDTA, and 1% NP-40). After the incubation, the beads were washed with TNE buffer and the bound proteins were separated by SDS-PAGE. The $^{35}$S signal was amplified using Amplify (Amersham) and exposed on x-ray film.

CARD-3 Binds to p75 in Schwann Cells

To investigate if CARD-3 or RIP was expressed in Schwann cells, lysates were collected from freshly isolated Schwann cells grown for different times and then immuno-blotted with an antibody directed to against CARD-3, RIP or p75 (FIG. 5A). The immunoblot shows that both CARD-3 and RIP are highly expressed in newly dissociated cultures of Schwann cells, but CARD-3 was no longer expressed in cultures of 30 days or more. As expected, p75 receptor expression was also induced and maintained in these Schwann cell cultures.

To identify if either CARD-3 or RIP could interact with p75, 293 cells were co-transfected with cDNAs encoding the p75 receptor and epitope tagged CARD-3 or RIP. Lysates were immunoprecipitated for either CARD-3 or RIP, and immunoblotted for p75. Antibodies against RIP were unable to immunoprecipitate p75, however a strong association between CARD-3 and the p75 receptor was detected (FIG. 5B). This transfection experiment indicates that CARD-3, and not RIP, associated with p75.

Figure 6:
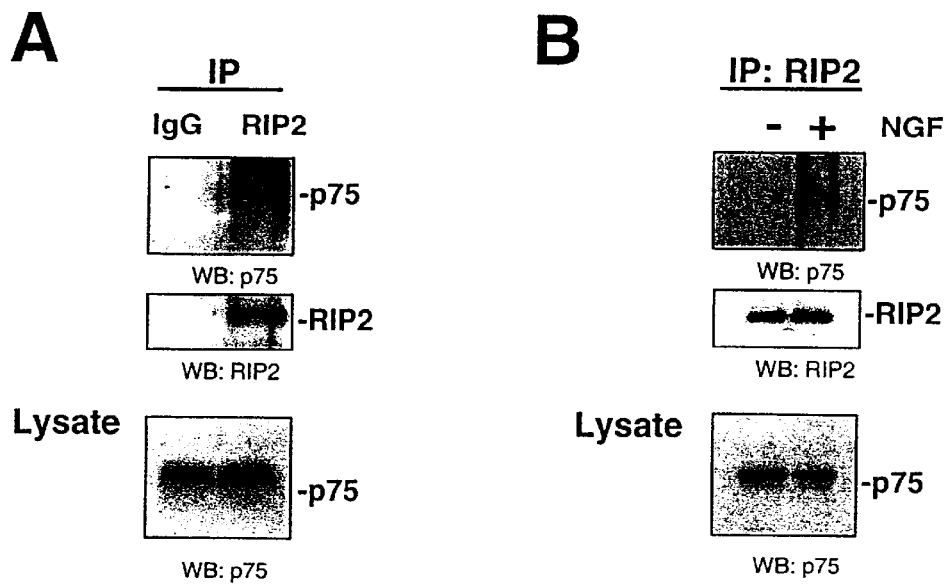
FIGS. 6A and 6B depict results of immunoblot analysis showing that the interaction between p75 and CARD-3 is enhanced by NGF.

To determine if this interaction is physiologically relevant, we assessed whether endogenous CARD-3 protein interacted with p75 in Schwann cells. Lysates were collected from dissociated cultures and immunoprecipitated with either anti-CARD-3 or normal rabbit IgG and immunoblotted for p75. Incubation with anti-CARD-3 antibody resulted in immunoprecipitation of p75 receptors (FIG. 6A). As a control, normal IgG did not produce a positive signal for p75. This immunoprecipitation experiment demonstrates an endogenous interaction exists between CARD-3 and p75 in Schwann cells from the sciatic nerve. Moreover, Schwann cell cultures treated with NGF yielded an association of p75 and CARD-3, indicating that this interaction was dependent upon the presence of NGF (FIG. 6B).

CARD-3 Binds to the p75 Death Domain

To determine if CARD-3 binds directly to p75, the CARD-3 protein was translated in vitro with $^{35}$S-methionine and then incubated with GST-fusion proteins containing the intracellular domain (IC) or the death domain (DD) of p75. GST-p75 fusion proteins were isolated and incubated with $^{35}$S-labeled CARD-3. Whereas CARD-3 did not bind to GST alone, an interaction was observed with both the GST-p75 intracellular and death domain constructs (FIG. 7A), suggesting a direct association between CARD-3 and the death domain of p75.

Figure 7:
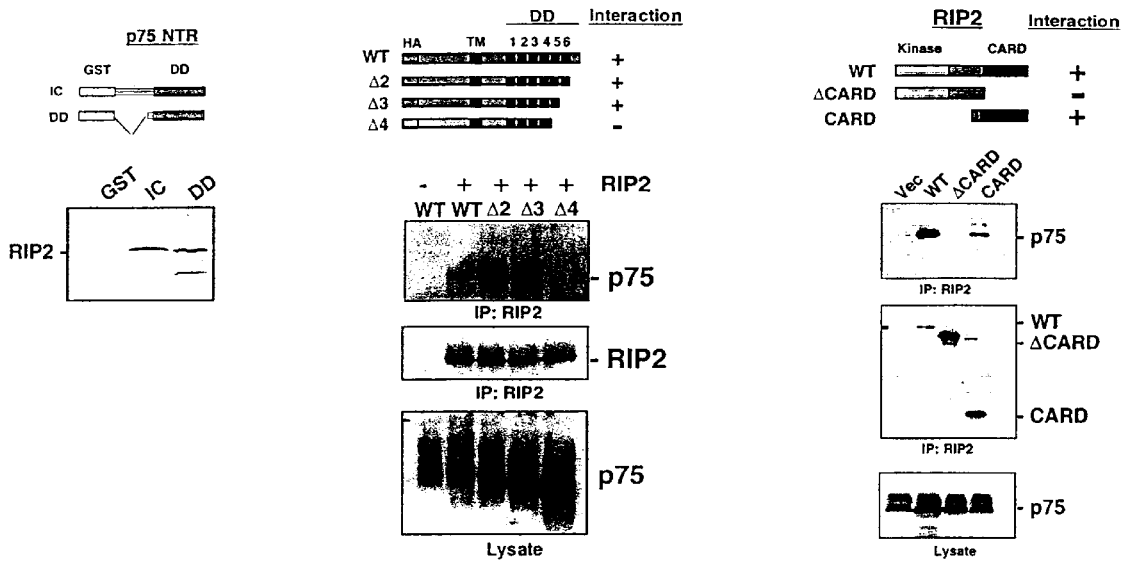
FIGS. 7A, 7B, and 7C depict the results of experiments demonstrating that the CARD of CARD-3 binds to the death domain of p75.

To map the binding domains between CARD-3 and p75 further, 293 cells were transfected with CARD-3 and serial deletions of HA-epitope tagged-p75 receptor. The lysate were immunoprecipitated for myc-CARD-3 and immunoblotted with a polyclonal anti-HA to detect the p75 proteins. Each protein was monitored for expression following the transfection. In contrast to most of the p75 cytoplasmic deletions, CARD-3 did not bind to the Δ4 HA-p75 construct (FIG. 7B). This Δ4 domain represented the fifth α-helix in the death domain of p75. Hence, a main site of interaction of CARD-3 resides in the death domain of p75. Taken together, these experiments indicate that CARD-3 binds directly to p75 death domain.

RIP and CARD-3 proteins display considerable homology in the protein kinase and intermediate domains, but differ at the C-terminal region where RIP has a death domain and CARD-3 has a CARD domain. Because CARD-3, but not RIP, binds preferentially to p75, the CARD domain of CARD-3 may be important for the specificity of binding to p75. To verify the domain in CARD-3 that is important for binding to p75, a full length myc-CARD-3 (WT), a myc-CARD-3 missing the CARD domain (ΔCARD) and a myc-ΔARD-3 construct expressing only the CARD domain were co-transfected with p75 in 293 cells and analyzed for an association after immunoprecipitation (FIG. 7C). Deletion of the CARD domain eliminated the ability of CARD-3 to interact with p75, while a truncated CARD-3 containing the CARD domain still associated with p75. These experiments indicate that the CARD domain of CARD-3 is responsible for the binding to p75.

NGF Augments the Interaction of CARD-3 and p75 to Mediate NF-κB Activity

Figure 8:
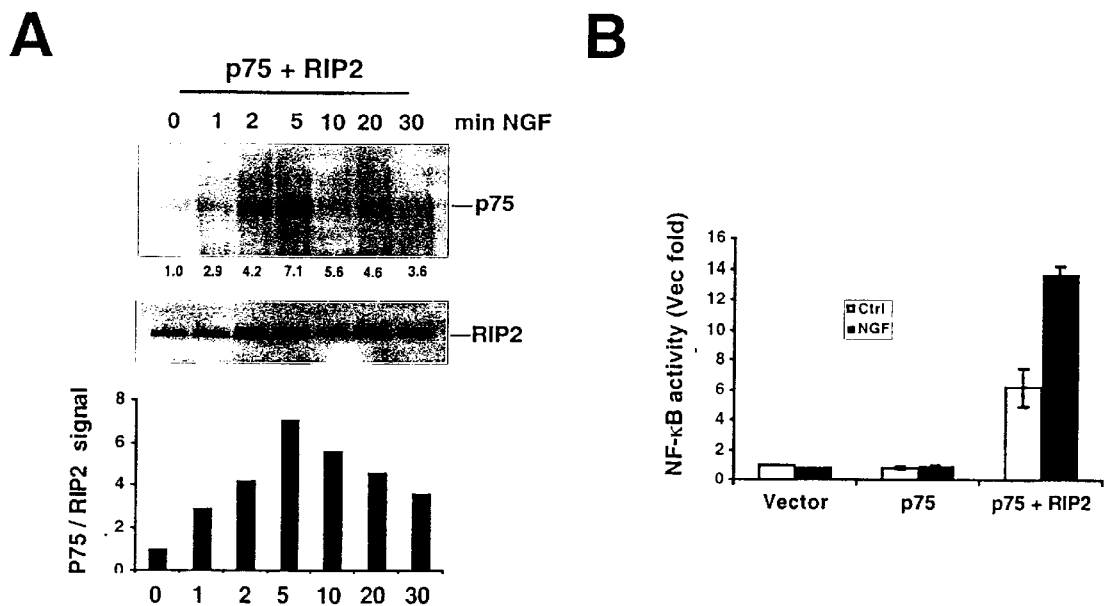
FIGS. 8A and 8B depict the results of experiments demonstrating that NGF induces NF-κB through CARD-3.

To verify the ligand dependency of the interaction between CARD-3 and p75, 293 cells were co-transfected with p75 and CARD-3 and treated with NGF for different times. The lysates were immunoprecipitated for CARD-3 and then immunoblotted for p75. As in the case of Schwann cells, addition of NGF augmented the interaction between CARD-3 and p75, peaking 5 minutes after NGF treatment (FIG. 8A). This experiment confirmed that CARD-3 interacted with the p75 receptor in an NGF-dependent manner.

Neurotrophins induce the NF-κB transcription factor, which plays an important role in preventing apoptosis in many cell types (Beg et al. (1996) *Science* 274:782; Lin et al. (1996) *Cell* 87:565). To test the possibility that CARD-3 is responsible for NGF-induced NF-κB activity, a NF-κB luciferase reporter construct was co-transfected in 293 cells with either p75, or the combination of p75 and CARD-3. After transfection the cells were incubated in low-serum with or without NGF for an additional 24 hrs. The cells were lysed and luciferase activity assessed as a measure of NF-κB activity. NGF did not induce NF-κB activity in cells transfected with p75 alone (FIG. 8B). However, in 293 cells co-transfected with both p75 and CARD-3, NGF produced a notable increase in NF-κB activity. This suggests that CARD-3 can mediate NGF induced NF-κB activity in the 293 cell expression system.

Regulation of NF-κB Activity in Schwann Cells

Figure 9:
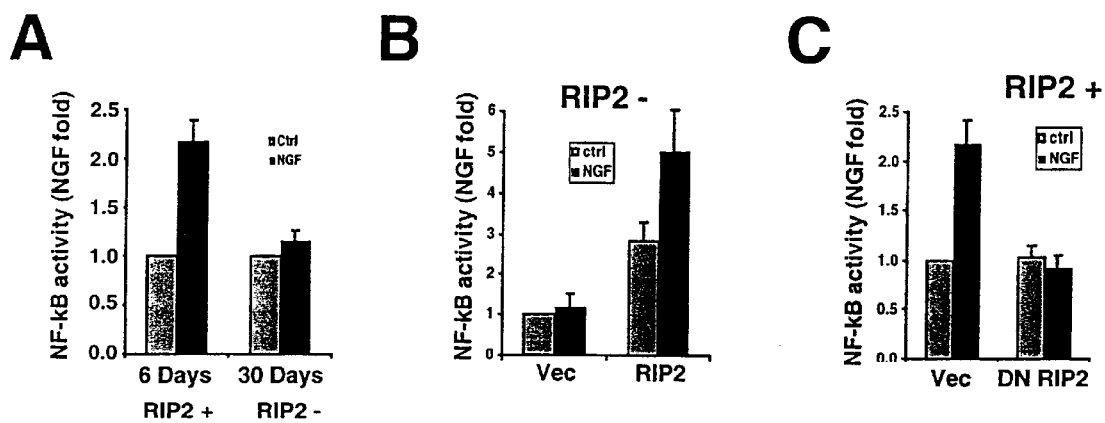
FIGS. 9A, 9B, and 9C depict the results of experiments demonstrating that CARD-3 mediates NGF-dependent NF-κB activity in Schwann cells.

To determine whether CARD-3 plays a role in NF-κB regulation in Schwann cells, the NF-κB luciferase reporter construct was transfected into Schwann cells isolated from P1 sciatic nerve. Cells cultured for five days were transfected and maintained under low-serum conditions for 24 hrs in the presence or absence of NGF. These cells express CARD-3 and p75 (FIG. 5A). In short-term cultures, NGF induced an increase in NF-κB activity in these cells (FIG. 9A). However, induction of NF-κB activity by NGF was not detected in the long-term cultures of 30 days or more. A loss of expression of CARD-3 in the long-term cultures (described above) was therefore correlated with the inability of NGF to activate NF-κB in long-term cultures. Thus, NGF induces NF-κB, but only in Schwann cells expressing CARD-3.

These findings establish two stages of Schwann cells, a short-term culture which is CARD-3+ and a long-term culture that is CARD-3−. To establish whether CARD-3 is necessary for NF-κB signaling in Schwann cells, CARD-3 was artificially expressed in long-term Schwann cells. Introduction of CARD-3 into these cells increased NF-κB activity 3-fold above background (FIG. 9B). Addition of NGF to the transfected Schwann cells increased NF-κB activity to an even higher level. These results indicated that expression of CARD-3 led to NF-κB activation in Schwann cells, and that the loss of CARD-3 was responsible for the inability of NGF to activate NF-κB activity.

Inhibition of CARD-3 Function

Figure 10:
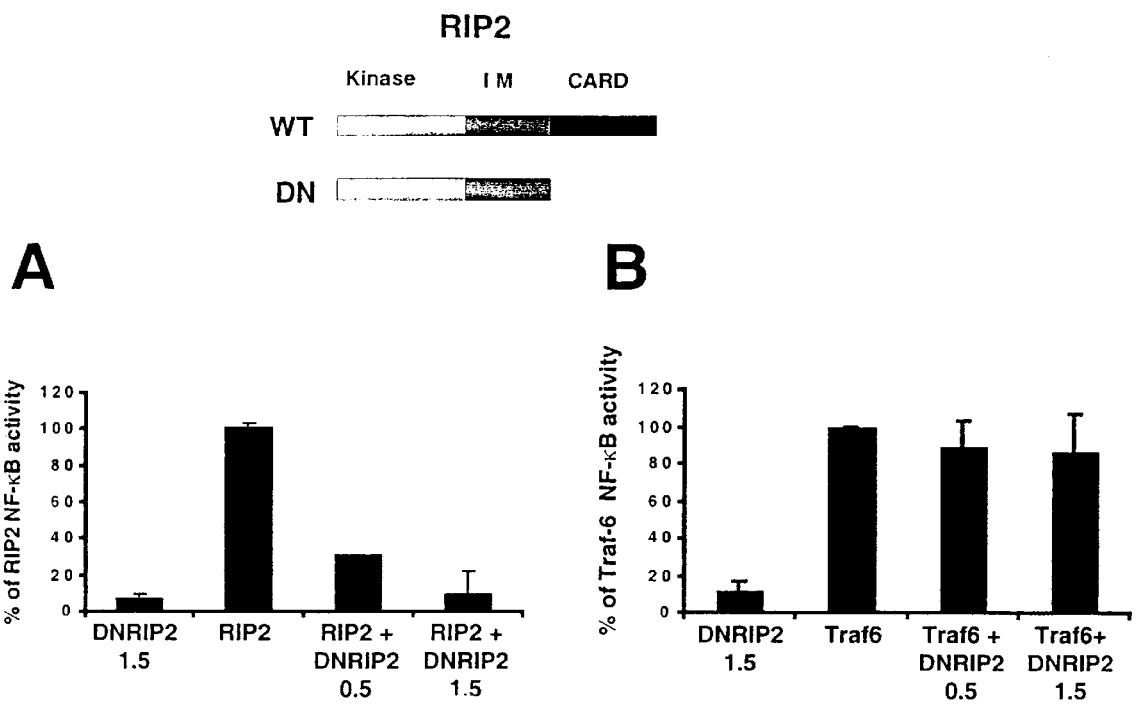
FIG. 10 depicts the results of an experiment demonstrating that a dominant negative CARD-3 mutant lacking a CARD domain blocks CARD-3 mediated NF-κB activity.

To establish more conclusively that CARD-3 is involved in p75 signaling, a dominant negative mutant was created based on the finding that both the CARD and protein kinase domains of CARD-3 are necessary for NF-κB activation. Thus, a CARD-3-CARD construct was created. Increasing amounts of this construct was co-expressed with wild type CARD-3 cDNA in 293 cells. The full length CARD-3 protein was equally expressed in all conditions. CARD-3-CARD (referred to as DN CARD-3) reduced the ability of CARD-3 WT to activate NF-κB in a dose dependent way, while DN CARD-3 itself did not activate NF-κB (FIG. 10A).

As a control, the effect of DN CARD-3 on TRAF-6 activation of mediate NF-κB was examined. TRAF-6, and activator of NF-κB is unrelated to CARD-3, and the DN CARD-3 dominant negative mutant should have no effect. Indeed, expression of DN CARD-3 did not reduce the ability of TRAF6 to induce NF-κB (FIG. 10B). These results indicate that expression of the dominant negative CARD-3 blocked NF-κB activity through CARD-3, and not other adaptor molecules.

Blocking CARD-3 Function in Schwann Cells

To determine the functional consequences of inhibiting CARD-3 in Schwann cells, a NF-κB luciferase reporter and the DN CARD-3 cDNA was introduced in freshly dissociated Schwann cells (CARD-3+). After transfection, cells were incubated with low serum with or without NGF for 24 hrs and NF-κB activity was measured. Consistent with previous observations, NGF induced an increase in NF-κB activity (FIG. 9C). Expression of DN CARD-3 blocked NGF dependent NF-κB activation. This result demonstrates that inhibition of CARD-3 function specifically blocks ligand-dependent induction of NF-κB in Schwann cells.

Influence of CARD-3 on NGF-dependent Cell Death

Figure 11:
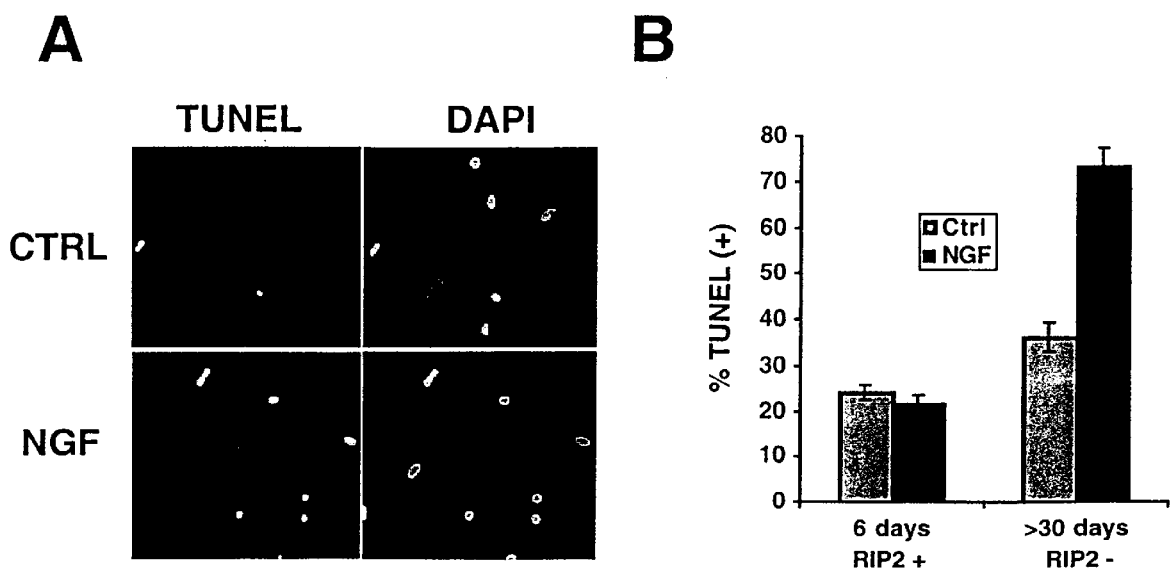
FIGS. 11A and 11B depict the results of experiments demonstrating that NGF can induce apoptosis in Schwann cells.

To determine the role of CARD-3 expression in primary Schwann cells, the viability of Schwann cells grown at early and later times in culture was investigated. NGF treated and untreated Schwann cells were fixed and assessed for TUNEL immunoreactivity (FIG. 11A). In the 6-day CARD-3+ cultures, 25% of the cells were found to be TUNEL positive. Addition of NGF did not exhibit a detectable change (FIG. 11B). Analysis of 30-day CARD-3-cultures indicated there was a higher background of cell death (35%). However, unlike the 6-day culture, NGF increased the number of TUNEL-positive cells 2-fold. These findings indicate NGF induced cell death preferentially in Schwann cells that do not express CARD-3.

Because CARD-3 association with p75 can increase NF-κB activity, CARD-3 might protect Schwann cells from apoptosis. To assess the effects of endogenous CARD-3, DN CARD-3 was co-transfected with GFP and the viability of CARD-3+cells was assessed. After transfection, the cells were incubated in low serum for 18–24 hrs with or without NGF. GFP expressing cells were identified and characterized for apoptotic morphology, including nuclear condensation and the presence of apoptotic bodies (FIG. 12A).

Figure 12:
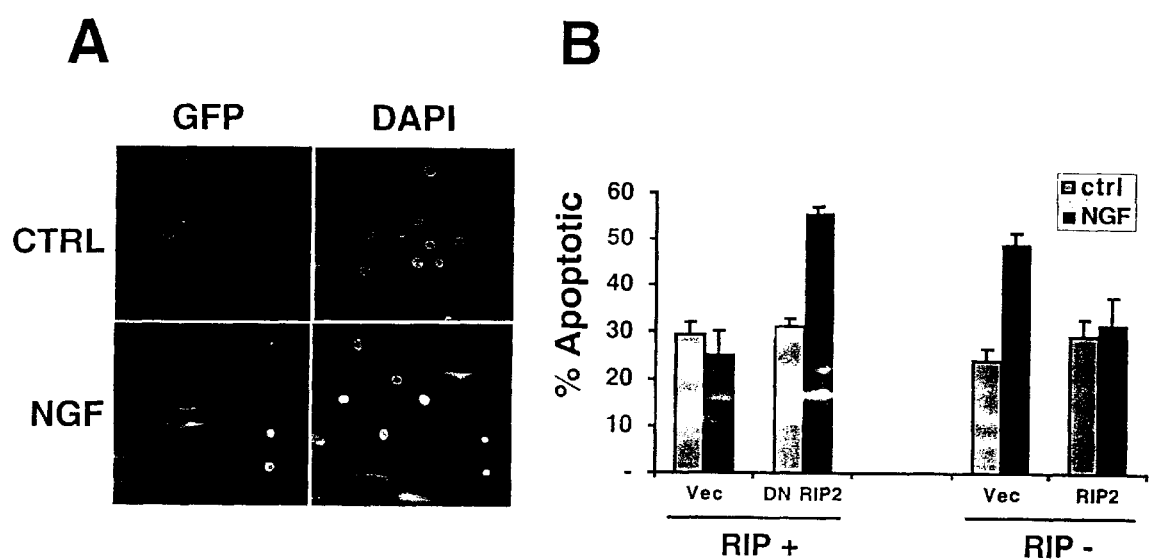
FIGS. 12A and 12B depict the results of experiments demonstrating that CARD-3 can block NGF-induced apoptosis in Schwann cells.

Cells co-transfected with the DN CARD-3 construct resulted in a marked increase in the number of apoptotic cells after NGF treatment (FIG. 12B). In contrast, transfection of a vector control did not produce an increase in cell death by NGF, which was similar to the TUNEL results (FIG. 11B). The cell death measurements together with the NF-κB responses indicate that inhibition of endogenous CARD-3 function in RIP+ Schwann cells blocks NGF mediated NF-κB activity and leads to an increased NGF induced cell death (FIG. 12B).

Since NGF increases CARD-3 binding to p75 and NF-κB activation, the effect f of artificially expressing CARD-3 in long term CARD-3-deficient Schwann cells was investigated. Briefly, CARD-3 was co-transfected with GFP into long-term cultured Schwann cells. As before, apoptotic morphology was followed in the GFP expressing cells. Compared to vector transfected cells, expression of CARD-3 negated the NGF killing effect (FIG. 12B). The protection of cells from NGF-induced cell death by CARD-3 expression indicated that transcriptional events through NF-κB play an important role in regulating Schwann cell survival.

Role of CARD-3 in Mediating NGF Response

The experiments described above demonstrate that: CARD-3 interacts with p75 and regulates the ability of NGF to regulate survival decisions, that the interaction between CARD-3 and p75 was observed endogeneously in Schwann cells, that NGF augments the interaction between CARD-3 and p75 and enhances CARD-3 mediated NF-κB activity both in 293 and Schwann cells, that artificially expressed CARD-3 promotes NGF-induced NF-κB activity and protects long-term cultured Schwann cells from NGF induced cell death, and that inhibiting CARD-3 in early Schwann cells leads to NGF induced cell death. The results demonstrate that p75 can initiate two separate pathways at the same time, NF-κB and cell death and that CARD-3 plays a key role in NGF function in Schwann cells by leading to the activation of NF-κB and negating death signals from p75.

Significantly, the interaction of CARD-3 with p75 is ligand dependent, in contrast to other TNF members, such as CD40 and TNF receptor. Previous overexpression studies with RIP or CARD-3 in heterologous cells yielded enhanced apoptosis, in addition to NF-κB (Inohara et al. (1998) *J. Biol. Chem.* 273:12296; McCarthy et al. (1998) *J. Biol. Chem.* 273:16968). Strikingly, in Schwann cells, CARD-3 expression does not lead to an apoptotic outcome, but rather to a pro-survival function.

The studies described above demonstrate that the CARD domain of CARD-3 interacts with the death domain of p75. Most CARD-containing proteins are directly involved in the apoptotic pathway. These include caspases and Apaf-1 (Hofman et al. (1997) *TIBS* 22:155). The death domain mediates protein-protein interactions and is essential for the transduction of cytotoxic signals (Feinstein et al. (1995) *TIBS* 20:342). In contrast, as the experiments described above suggest, that death domain of p75 can play a protective role in Schwann cells through binding to a CARD protein, CARD-3. Previous analysis of the death domain of p75 indicated a different mode of action compared to the TNF and Fas receptors (Gu et al. (1999) *J. Neuroscience* 19:3043; Kong et al. (1999) *Cell Death Differ.* 6:1133). This conclusion is consistent with recent microinjection experiments in sensory neurons, in which the death domain of p75 was excluded from apoptotic signaling (Coulson et al. (2000) *J. Biol. Chem.* 275:30537). Instead, a twenty-nine amino acid segment of the p75 juxtamembrane region was responsible for cell killing properties. The effects of CARD-3 in binding the death domain of p75 and providing an anti-apoptotic response in Schwann cells is compatible with the results from sensory neurons (Coulson et al. (2000), supra).

The ability of Schwann cells to receive survival signals is relevant to events observed in vivo during development and axonal injury. One of the earliest responses is an elevated level of expression of NGF and the p75 neurotrophin receptor in Schwann cells (Lemke et al. (1988) supra; Taniuchi et al. (1988) supra). Expression of p75 is closely associated with Schwann cell development. Historically, presentation or sequestration of neurotrophins has been proposed for p75 receptors, however, there is little direct evidence for this function. On the other hand, migration of Schwann cells has been shown to be dependent upon p75 receptors (Anton et al. (1994) supra; Bentley et al. (2000) supra). More recently, specific neurotrophins such as NGF stimulate JNK and NF-κB pathways, leading to the possibility that viability of Schwann cells may be regulated by neurotrophins. Indeed, Schwann cells undergo apoptotic cell death during development and after trophic factor withdrawal (Soilu-Hanninen et al. (1999) supra; Syroid et al. (2000) supra).

During the first week of injury, Schwann cells are highly proliferative and express high levels of NGF and p75. This establishes an autocrine mechanism for NGF to signal through p75 in the absence of axons (Grinspan et al. (1996) *J. Neuroscience* 16:6107; Jessen et al. (1999) *Trends Neuroscience* 22:402). An NGF increase in NF-κB activity in the distal Schwann cells following a sciatic nerve injury may protect Schwann cells from early cell death. Indeed, an increase in NF-κB in distal Schwann cells following a sciatic nerve crush model has been observed (Dobrowsky et al. (2000) *J. Neurosci. Res.*61:237; Frostick et al. (1998) *Microsurgery* 18:397). At later times after a nerve lesion, if regeneration or axonal contact has not occurred, Schwann cell death increases significantly (Ferri et al. (1999) *Neurosci. Lett.* 272:191). One explanation to account for these apoptotic events involves p75 signaling. The dual role of p75 signaling during nerve injury may depend upon CARD-3.

It has been suggested that TRAF proteins mediate p75 induced NF-κB activity (Khursigara et al. (1999) *J. Biol. Chem.* 274:2597; Ye et al. (1999) *J. Biol. Chem.* 274:30202). In fact, expression of a dominant negative form of TRAF6 blocked NF-κfunctions (Foehr et al. (2000) *J. of Neuroscience* 20:7556; Khursigara et al. (1999) supra). Thus, TRAF and CARD-3 may both mediated p75. First, TRAF proteins may be acting downstream of CARD-3, or in concert with CARD-3. In vitro binding data indicates that TRAF proteins can bind to CARD-3 and dominant negative TRAF proteins block CARD-3 activation of NF-κB (McCarthy et al. (1998) supra). Recent experiments indicate that the p55 TNF receptor requires both TRAF2 and RIP to induce NF-κB activity properly (Devin et al. (2000) *Immunity* 12:419). Second, dominant negative forms of TRAF proteins can bind to the NF-κB inducing kinase (NIK) of IKK enzymes and inhibit the subsequent activation of NF-κB. Third, TRAF6 competes with CARD-3 in binding to p75. As a result of overexpression of TRAF6, CARD-3-p75 interaction are decreased (data not shown). This result suggests there may be complexes of TRAF and CARD-3 proteins with the p75 receptor, in addition to other proteins.

Other adaptor proteins that bind to p75 have been reported recently. Three different proteins, NRIF (Casademunt et al. (1999) *EMBO J.* 18:6050), NADE (Mukai et al. (2000) *J. Biol. Chem.* 275:17566) and NRAGE (Salehi et al. (2000) *Neuron* 27:279), bind sequences in the cytoplasmic domain of the p75 receptor and each contributes to apoptosis in immortalized cell lines, or are correlated with neurotrophin dependent cell death. CARD-3 may interfere with the binding of these proteins to p75 or exert an effect upon downstream apoptotic signaling through these proteins. Still other adaptor proteins, including RhoA GTPase (Yamashita et al. (1999) *Neuron* 24:585) and the zinc finger protein SC-1 (Chittka et al. (1999) *Proc. Nat'l. Acad. Sci. USA* 96:10705) exert non-apoptotic activities, such as neurite elongation and growth arrest.

Assays for Mediators of CARD-3 Activity

Mediators of the interaction between CARD-3 and p75 can be identified by exposing cells expressing p75 (or a death domain containing fragment thereof) and CARD-3 (or a CARD domain containing fragment thereof) to a selected compound and measuring the binding of p75 to CARD-3. This assay can be performed in the presence or absence of NGF. Binding can be measured in a number of ways. For example, antibodies against CARD-3 (or p75) can be used to precipitate CARD-3 (or p75) and the presence of p75 (or CARD-3) in the precipitated material can be measured. Similar assays can be performed in vitro using purified proteins. Alternatively, a two-hybrid assay can be used to measure the interaction.

Mediators of CARD-3 activity can also be identified by expressing CARD-3 and a NF-κB reporter in cells, e.g., Schwann cells, and measuring NF-κB activity in the presence and absence of NGF. In addition, apoptosis induced by NGF can be measured in the presence and absence of CARD-3 (or a CARD domain containing fragment thereof) to identify specific modulators of CARD-3 mediated apoptosis.

The invention features a method for determining whether a test compound alters the binding of CARD-3 to p75, comprising: a) measuring the binding of a polypeptide comprising the CARD domain of CARD-3 to a polypeptide comprising the death domain of p75 in the presence of a test compound; b) measuring the binding of a polypeptide comprising the CARD domain of CARD-3 to a polypeptide comprising the death domain of p75 in the absence of the test compound; and c) determining that the test compound alters the binding of CARD-3 to p75 if the binding measured in step a) differs from that measured in step b). The binding can be in vitro binding or in vivo binding. For example, one of the polypeptides can be attached to solid support and the binding can be measured. Alternatively, the cells which naturally or recombinantly express both polypeptides. A sample of the cells is exposed to the test compound for a period of time. The cells are then lysed and the interaction between the two polypeptides is measured by, for example, contacting the cell lysate with an antibody which selectively binds to one of the polypeptides, isolating the antibody-polypeptide complexes, and then determining if the other polypeptide is isolated with the complexes.

The polypeptide comprising the CARD domain of CARD-3 can be a full-length CARD-3 polypeptide. The polypeptide comprising the death domain of p75 can be a full-length $p^{75}$ polypeptide.

The invention also features a method for determining whether a test compound alters the binding of CARD-3 to p75, comprising: a) measuring the binding of CARD-3 to p75 in a sample comprising cells in the presence of a test compound; b) measuring the binding of CARD-3 to p75 in a sample comprising cells in absence of the test compound.; and determining that the test compound alters the binding of CARD-3 to p75 if the binding measured in step a) differs from that measured in step b). The cells can be, e.g., neuronal cells or Schwann cells. The cells can express NGF.

The invention also features a method for determining whether a test compound alters CARD-3 mediated NF-κB activity, comprising: a) measuring the effect of the test compound on NF-κB activity in a cell that expresses CARD-3; b) measuring the effect of the test compound on NF-κB activity in a cell that does not express CARD-3; and c) determining that the test compound alters CARD-3 mediated NF-κB activity when the effect measured in step a) is greater than the effect measured in step b). The cells can be neuronal cells, e.g., Schwann cells.

The invention features a method for determining whether a test compound inhibits the kinase activity of CARD-3, comprising: a) measuring the phosphorylation of a CARD-3 substrate by CARD-3 in the absence of a test compound; b) measuring the phosphorylayion of a CARD-3 substrate by CARD-3 in the presence of a test compound; and c) determining that the test compound inhibits the kinase activity of CARD-3 when the phosphorylation measured in step b) is less than the phosphorylation measure in step a).

The invention also features a method for determining whether a test compound alters CARD-3 mediated apoptosis, comprising: a) measuring the effect of a test compound on apoptosis of cells expressing CARD-3; b) measuring the effect of the test compound on apoptosis of cells that do not express CARD-3; and c) determining that the test compound alters CARD-3 mediated apoptosis when the effect measured in step a) is greater than the effect measured in step b). The cells can be neuronal cells, e.g., Schwann cells.

I. Nucleic Acid Molecules Encoding CARD-3 or CARD-4

The card-3 or card-4 nucleic acid molecules of the invention can be cDNA, genomic DNA, synthetic DNA, or RNA, and can be double-stranded or single-stranded. In the event the nucleic acid molecule is single-stranded, it can be either a sense or an antisense strand. Fragments of these molecules are also considered within the scope of the invention, and can be produced, for example, by the polymerase chain reaction (PCR), or generated by treating a longer fragment (e.g., a full-length card-3 or card-4 gene sequence) with one or more restriction endonucleases. Similarly, a full-length card-3 or card-4 RNA molecule, or a fragment thereof, can be produced by in vitro transcription. The isolated nucleic acid molecule of the invention can encode a fragment of CARD-3 or CARD-4 that is not found as such in the natural state. Although nucleic acid molecules encoding any given fragment of CARD-3 or CARD-4 are within the scope of the invention, fragments that retain the biological activity of CARD-3 or CARD-4 are preferred.

The nucleic acid molecules of the invention encompass recombinant molecules, such as those in which a nucleic acid molecule (e.g., an isolated nucleic acid molecule encoding CARD-3 or CARD-4, or a fragment thereof) is incorporated: (1) into a vector (e.g., a plasmid or viral vector), (2) into the genome of a heterologous cell, or (3) into the genome of a homologous cell, at a position other than the natural chromosomal location. Recombinant nucleic acid molecules, transgenic animals, and uses therefor are discussed further below.

In addition to nucleic acids encoding full-length CARD-3 polypeptides, the invention encompasses nucleic acid sequences encoding full-length CARD-4 polypeptides. Such DNA sequences can be isolated by techniques widely known in the art. For example, oligonucleotide probes can be designed corresponding to the known partial CARD-4 amino acid sequence described herein (FIG. 3, SEQ ID NO:3) and used to screen by hybridization cDNA or genomic DNA libraries prepared from card-4-expressing tissue (e.g., by the methods described in Sambrook et al., Molecular Cloning: A Laboratory Manual, 2nd ed., Cold Spring Harbor., 1989). Alternatively, anti-CARD-4 antibodies can be used to screen expression libraries prepared from the mRNA of cells expressing card-4 in order to obtain card-4 cDNAs (Sambrook et al., supra). Preferably, any osteometrin cDNA or genomic DNA is cloned by PCR using degenerate primers corresponding to the partial amino acid sequences of CARD-4. Overlapping partial cDNAs or genomic DNA clones are used to derive the full length clones by any method known in the art, e.g., PCR.

The nucleic acid molecules of the invention can contain naturally occurring sequences, or sequences that differ from those that occur naturally, but, due to the degeneracy of the genetic code, encode the same polypeptide. In addition, the nucleic acid molecules of the invention are not limited to those that encode the amino acid residues of the CARD-3 or CARD-4 polypeptide encoded by SEQ ID NOs 1 and 3, respectively; they can also include some or all of the non☐ coding sequences that lie upstream or downstream from a card-3 or card-4 coding sequence, a heterologous regulatory element, or a sequence encoding a heterologous polypeptide (e.g., a reporter gene). Regulatory elements and reporter genes are discussed further below.

The nucleic acid molecules of the invention can be synthesized (for example, by phosphoramidite-based synthesis) or obtained from a biological cell, such as the cell of a mammal. Thus, the nucleic acids can be those of a human, mouse, rat, guinea pig, cow, sheep, goat, horse, pig, rabbit, monkey, dog, or cat. Combinations or modifications of the nucleotides within these types of nucleic acid molecules are also encompassed.

In the event the nucleic acid molecules of the invention encode or act as antisense molecules, they can be used, for example, to regulate translation of card-3 or card-4 mRNA. Techniques associated with detection of nucleic acid sequences or regulation of their expression are well known to persons of ordinary skill in the art, and can be used in the context of the present invention to diagnose or treat disorders associated with aberrant card-3 or card-4 expression. However, aberrant expression of card-3 or card-4 (or aberrant activity of CARD-3 or CARD-4) is not a prerequisite for treatment according to the methods of the invention; the molecules of the invention (including the nucleic acid molecules described here) are expected to be useful in improving the symptoms associated with a variety of medical conditions regardless of whether or not the expression of card-3 or card-4 (or the activity of CARD-3 or CARD-4) is detectably aberrant. Nucleic acid molecules are discussed further below in the context of their clinical utility.

The invention also encompasses nucleic acid molecules that encode other members of the card-3 or card-4 family (e.g., other mammalian homologues of card-3 or card-4). Such nucleic acid molecules will be readily identified by their ability to hybridize under stringent conditions to a nucleic acid molecule encoding a CARD-3 or CARD-4 polypeptide (e.g., nucleic acid molecules having the sequence of SEQ ID NO:2 or SEQ ID NO:4). The cDNA sequences described herein (SEQ ID NO:2 and SEQ ID NO:4) can be used to identify these nucleic acids, which include, for example, nucleic acids that encode homologous polypeptides in other species, splice variants of the card-3 or card-4 gene in humans or other mammals, allelic variants of the card-3 or card-4 gene in humans or other mammals, and mutant forms of the card-3 or card-4 gene in humans or other mammals.

The preferred class of nucleic acid molecules that hybridize to SEQ ID NO:2 and SEQ ID NO:4 are nucleic acid molecules that encode human allelic variants of CARD-3 or CARD-4. There are two major classes of such variants: active allelic variants, naturally occurring variants that have the biological activity of CARD-3 or CARD-4 and non-active allelic variants, naturally occurring allelic variants that lack the biological function of CARD-3 or CARD-4. Active allelic variants can be used as an equivalent for a CARD-3 or CARD-4 protein having the amino acid sequence encoded by SEQ ID NO:1 and SEQ ID NO:3 or as described herein whereas nonactive allelic variants can be used in methods of disease diagnosis and as a therapeutic target.

The invention features methods of detecting and isolating such nucleic acid molecules. Using these methods, a sample (e.g., a nucleic acid library, such as a cDNA or genomic library) is contacted (or "screened") with a card-3 or card-4☐specific probe (e.g., a fragment of SEQ ID NO:4 that is at least 17 nucleotides long). The probe will selectively hybridize to nucleic acids encoding related polypeptides (or to complementary sequences thereof). The term "selectively hybridize" is used to refer to an event in which a probe binds to nucleic acid molecules encoding CARD-3 or CARD-4 (or to complementary sequences thereof) to a detectably greater extent than to nucleic acids encoding other polypeptides, particularly other types of CARD-containing molecules (or to complementary sequences thereof). The probe, which can contain at least 17 nucleotides (e.g., 18, 20, 25, 50, 100, 150, or 200 nucleotides) can be produced using any of several standard methods (see, e.g., Ausubel et al., Current Protocols in Molecular Biology, Vol. I, Green Publishing Associates, Inc., and John Wiley & Sons, Inc., NY, 1989). For example, the probe can be generated using PCR amplification methods in which oligonucleotide primers are used to amplify a CARD-3 or CARD-4☐specific nucleic acid sequence that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the double helix). Complete complementarity between the hybridizing regions is not required in order for a duplex to form; it is only necessary that the number of paired bases is sufficient to maintain the duplex under the hybridization conditions used.

Typically, hybridization conditions initially used to identify related genes are of low to moderate stringency. These conditions favor specific interactions between completely complementary sequences, but allow some non☐specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (e.g., room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (e.g., the content of purine-like nucleotides versus the content of pyrimidine-like nucleotides) and the type of nucleic acid (e.g., DNA or RNA) affect hybridization. An additional consideration is whether one of the nucleic acids is immobilized (e.g., on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acid molecules are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50EC in Church buffer (7% SDS, 0.5% NaHPO4, 1 M EDTA, 1% BSA) and washing is carried out at 50EC in 2×SSC.

Preferably, nucleic acid molecules of the invention that are defined by their ability to hybridize with nucleic acid molecules having the sequence shown in SEQ ID NO:2 and SEQ ID NO:4 or under stringent conditions will have additional features in common with card-3 or card-4. For example, the nucleic acid molecules identified by hybridization may have a similar, or identical, expression profile as the card-3 or card-4 molecules described herein, or may encode a polypeptide having one or more of the biological activities possessed by CARD-3 or CARD-4.

Once detected, the nucleic acid molecules can be isolated by any of a number of standard techniques (see, e.g., Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing card-3 or card-4-related coding sequences and/or their complements (i.e., "antisense" sequence) and fragments thereof; (b) expression vectors that contain any of the foregoing card-3 or card-4-related sequences operatively associated with a regulatory element (examples of which are given below) that directs the expression of the coding sequences; (c) expression vectors containing, in addition to sequences encoding a CARD-3 or CARD-4 polypeptide, nucleic acid sequences that are unrelated to nucleic acid sequences encoding CARD-3 or CARD-4, such as molecules encoding a reporter or marker; and (d) genetically engineered host cells that contain any of the foregoing expression vectors, and thereby express the nucleic acid molecules of the invention in the host cell. The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, and the promoters of the yeast α-mating factors.

Additionally, the CARD-3 or CARD-4 encoding nucleic acid molecules of the present invention can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neor, G418r), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, a chimeric or hybrid polypeptide of the invention will include a first portion and a second portion; the first portion being a CARD-3 or CARD-4 polypeptide or a fragment thereof (preferably a biologically active fragment) and the second portion being, for example, the reporter described above or an immunoglobulin constant region.

The expression systems that can be used for purposes of the invention include, but are not limited to, microorganisms such as bacteria (e.g., E. coli and B. subtilis) transformed with recombinant bacteriophage DNA, plasmid DNA, or cosmid DNA expression vectors containing the nucleic acid molecules of the invention; yeast (e.g., Saccharomyces and Pichia) transformed with recombinant yeast expression vectors containing the nucleic acid molecules of the invention, preferably containing a nucleic acid sequence encoding all or a portion of CARD-3 or CARD-4 (such as the sequence of SEQ ID NO:2 or SEQ ID NO:4); insect cell systems infected with recombinant virus expression vectors (e.g., baculovirus) containing a nucleic acid molecule of the invention; plant cell systems infected with recombinant virus expression vectors (e.g., cauliflower mosaic virus [CaMV] and tobacco mosaic virus [TMV]) or transformed with recombinant plasmid expression vectors (e.g., Ti plasmid) containing card-3 or card-4 nucleotide sequences; or mammalian cell systems (e.g., COS, CHO, BHK, 293, VERO, HeLa, MDCK, WI38, and NIH 3T3 cells) harboring recombinant expression constructs containing promoters derived from the genome of mammalian cells (e.g., the metallothionein promoter) or from mammalian viruses (e.g., the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing CARD-3 or CARD-4 polypeptides or for raising antibodies to those polypeptides, vectors that are capable of directing the expression of high levels of fusion protein products that are readily purified may be desirable. Such vectors include, but are not limited to, the E. coli expression vector pUR278 (Ruther et al., EMBO J 2:1791 [1983]), in which the coding sequence of the insert may be ligated individually into the vector in frame with the lacZ coding region so that a fusion protein is produced; pIN vectors (Inouye and Inouye, Nucl Acids Res 13:3101 [1985]; and Van Heeke et al., J Biol Chem 264:5503 [1989]); and the like. pGEX vectors may also be used to express foreign polypeptides as fusion proteins with glutathione S☐transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhidrosis virus (AcNPV) can be used as a vector to express foreign genes. The virus grows in Spodoptera frugiperda cells. The coding sequence of the insert may be cloned individually into non-essential regions (e.g., the polyhedrin gene) of the virus and placed under control of an AcNPV promoter (e.g., the polyhedrin promoter). Successful insertion of the coding sequence will result in inactivation of the polyhedrin gene and production of non-occluded recombinant virus (i.e., virus lacking the proteinaceous coat encoded for by the polyhedrin gene). These recombinant viruses are then used to infect *Spodoptera frugiperda* cells in which the inserted gene is expressed (e.g., see Smith et al., J Virol 46:584 [1983]; and Smith, U.S. Pat. No. 4,215,051).

In mammalian host cells, a number of viral-based expression systems may be utilized. In cases where an adenovirus is used as an expression vector, the nucleic acid molecule of the invention can be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a CARD-3 or CARD-4 gene product in infected hosts (e.g., see Logan et al., Proc Natl Acad Sci USA 81:3655 [1984]). Specific initiation signals may also be required for efficient translation of inserted nucleic acid molecules. These signals include the ATG initiation codon and adjacent sequences. In cases where a complete gene or cDNA, including its own initiation codon and adjacent sequences, is inserted into the appropriate expression vector, no additional translational control signals may be needed. However, in cases where only a portion of the coding sequence is inserted (e.g., the portion encoding the mature form of a CARD-3 or CARD-4 protein) translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods Enzymol 153:516 [1987]).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. The mammalian cell types listed above are among those that could serve as suitable host cells.

For long-term, high-yield production of recombinant proteins, stable expression is preferred. For example, cell lines which stably express card-3 or card-4 can be engineered. Rather than using expression vectors that contain viral origins of replication, host cells can be transformed with DNA controlled by appropriate expression control elements (e.g., promoter sequences, enhancer sequences, transcription terminators, polyadenylation sites, etc.), and a selectable marker. Following the introduction of the foreign DNA, engineered cells can be allowed to grow for 1–2 days in an enriched media, and then switched to a selective media. The selectable marker in the recombinant plasmid confers resistance to the selection, and allows cells to stably integrate the plasmid into their chromosomes and grow to form foci which, in turn, can be cloned and expanded into cell lines. This method can advantageously be used to engineer cell lines that express card-3 or card-4. Such engineered cell lines may be particularly useful in screening and evaluating compounds that affect the endogenous activity of the gene product (i.e., CARD-3 or CARD-4).

A number of selection systems can be used. For example, the herpes simplex virus thymidine kinase (Wigler et al., Cell 11:223 [1977]), hypoxanthine-guanine phosphoribosyltransferase (Szybalska et al., Proc Natl Acad Sci USA 48:2026 [1962]), and adenine phosphoribosyltransferase (Lowy et al., Cell 22:817 [1980]) genes can be employed in tk-, hgprt- or aprt-cells, respectively. Also, anti☐metabolite resistance can be used as the basis of selection for the following genes: dhfr, which confers resistance to methotrexate (Wigler et al., Proc Natl Acad Sci USA 77:3567 [1980] and O'Hare et al., Proc Natl Acad Sci USA 78:1527 [1981]); gpt, which confers resistance to mycophenolic acid (Mulligan et al., Proc Natl Acad Sci USA 78:2072 [1981]); neo, which confers resistance to the aminoglycoside G-418 (Colberre-Garapin et al., J Mol Biol 150:1 [1981]); and hygro, which confers resistance to hygromycin (Santerre et al., Gene 30:147 [1984]).

Alternatively, any CARD-3 or CARD-4-containing fusion proteins can be readily purified utilizing an antibody specific for the fusion protein being expressed. For example, a system described by Janknecht et al. (Proc Natl Acad Sci USA 88:8972 [1991]) allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+☐nitriloacetic acid-agarose columns and histidine-tagged proteins are selectively eluted with imidazole-containing buffers.

As implied by the descriptions above, a host cell is any cell into which (or into an ancestor of which) a nucleic acid encoding a polypeptide of the invention (e.g., a CARD-3 or CARD-4 polypeptide) has been introduced by means of recombinant DNA techniques.

II. CARD-3 and CARD-4 Polypeptides

The CARD-3 or CARD-4 polypeptides described herein are those encoded by any of the nucleic acid molecules described above, and include fragments of CARD-3 or CARD-4, mutant forms of CARD-3 or CARD-4, active and non-active allelic variants of CARD-3 or CARD-4, splice variants of CARD-3 or CARD-4, truncated forms of CARD-3 or CARD-4, and fusion proteins containing all or a portion of CARD-3 or CARD-4. These polypeptides can be prepared for a variety of uses including, but not limited to, the generation of antibodies, as reagents in diagnostic assays, for the identification of other cellular gene products or exogenous compounds that can modulate the activity or expression of CARD-3 or CARD-4, and as pharmaceutical reagents useful for the treatment of any disorder in which the associated symptoms are improved by altering the activity of CARD-3 or CARD-4.

The terms "protein" and "polypeptide" are used herein to describe any chain of amino acid residues, regardless of length or post-translational modification (e.g., modification by glycosylation or phosphorylation). Thus, the term "CARD-3 or CARD-4 polypeptide" includes full-length, naturally occurring CARD-3 or CARD-4 polypeptides (that can be purified from tissues in which they are naturally expressed, according to standard biochemical methods of purification), as well as recombinantly or synthetically produced polypeptides that correspond either to a full-length, naturally-occurring CARD-3 or CARD-4 polypeptide or to particular domains or portions of such a polypeptide. The term also encompasses mature CARD-3 or CARD-4 having an added amino-terminal methionine (useful for expression in prokaryotic cells).

Preferred polypeptides are substantially pure CARD-3 or CARD-4 polypeptides that are at least 50% (e.g., 55%, 60%, or 65%), more preferably at least 70% (e.g., 72%, 75%, or 78%), even more preferably at least 80% (e.g., 80%, 85% or 90%), and most preferably at least 95% (e.g., 97% or even 99%) identical to SEQ ID NO:1 or SEQ ID NO:3. Those of ordinary skill in the art are well able to determine the percent identity between two amino acid sequences. Thus, if a polypeptide is encoded by a nucleic acid that hybridizes under stringent conditions with the card-3 or card-4 sequence disclosed herein and also encodes one or more of the conserved regions present in CARD-3 or CARD-4, it will be recognized as a CARD-3 or CARD-4 polypeptide and thereby considered within the scope of the present invention.

The invention also encompasses polypeptides that are functionally equivalent to CARD-3 or CARD-4. These polypeptides are equivalent to CARD-3 or CARD-4 in that they are capable of carrying out one or more of the functions of CARD-3 or CARD-4 in a biological system. Polypeptides that are functionally equivalent to CARD-3 or CARD-4 can have 20%, 40%, 50%, 75%, 80%, or even 90% of one or more of the biological activities of the full-length, mature human form of CARD-3 or CARD-4. Such comparisons are generally based on an assay of biological activity in which equal concentrations of the polypeptides are used and compared. The comparison can also be based on the amount of the polypeptide required to reach 50% of the maximal biological activity obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the Summary of the Invention.

Polypeptides that are functionally equivalent to CARD-3 or CARD-4 can be made using random mutagenesis techniques well known to those of ordinary skill in the art (and the resulting mutant CARD-3 or CARD-4 polypeptides can be tested for activity). It is more likely, however, that such polypeptides will be generated by site-directed mutagenesis (again using techniques well known to persons of ordinary skill in the art). These polypeptides may have increased functionality or decreased functionality.

To design functionally equivalent polypeptides, it is useful to distinguish between conserved positions and variable positions. This can be done by aligning the amino acid sequences of CARD-3 or CARD-4 that are obtained from various organisms (e.g., CARD-3 can be aligned with its murine homologue). Skilled artisans will recognize that conserved amino acid residues are more likely to be necessary for preservation of function. Thus, it is preferable that conserved residues are not altered.

Mutations within the card-3 or card-4 coding sequence can be made to generate variant card-3 or card-4 genes that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N□X□S or N□X-□), and/or an amino acid deletion at the second position of any one or more of such recognition sequences, will prevent glycosylation at the modified tripeptide sequence (see, e.g., Miyajima et al., EMBO J 5:1193 [1986]).

The polypeptides of the invention can be expressed fused to another polypeptide, for example, a marker polypeptide or fusion partner. For example, the polypeptide can be fused to a hexa-histidine tag to facilitate purification of bacterially expressed protein or a hemagglutinin tag to facilitate purification of protein expressed in eukaryotic cells. In addition, a CARD-3 or CARD-4 polypeptide can be fused to GST.

The polypeptides of the invention can be chemically synthesized (e.g., see Creighton, "Proteins: Structures and Molecular Principles," W. H. Freeman & Co., NY, 1983), or, perhaps more advantageously, produced by recombinant DNA technology as described herein. For additional guidance, persons of ordinary skill in the art may consult Ausubel et al. (supra), Sambrook et al. (supra), and, particularly for examples of chemical synthesis, Gait, Oligonucleotide Synthesis, IRL Press, Oxford (1984).

III. Transgenic Animals

CARD-3 or CARD-4 polypeptides can also be expressed in transgenic animals. Such transgenic animals represent model systems for the study of disorders that are either caused by or exacerbated by abnormal expression of card-3 or card-4, or disorders that can be treated by altering the expression of card-3 or card-4 or the activity of CARD-3 or CARD-4 (even though the expression or activity is not detectably abnormal). Transgenic animals can also be used for the development of therapeutic agents that modulate the expression of card-3 or card-4 or the activity of CARD-3 or CARD-4.

Transgenic animals can be farm animals (e.g., pigs, goats, sheep, cows, horses, rabbits, and the like) rodents (such as rats, guinea pigs, and mice), non□human primates (e.g., baboons, monkeys, and chimpanzees), and domestic animals (e.g., dogs and cats). Transgenic mice are especially preferred.

Any technique known in the art can be used to introduce a card-3 or card-4 transgene into animals to produce founder lines of transgenic animals. Such techniques include, but are not limited to, pronuclear microinjection (U.S. Pat. No. 4,873,191); retrovirus mediated gene transfer into germ lines (Van der Putten et al., Proc Natl Acad Sci USA 82:6148 [1985]); gene targeting into embryonic stem cells (Thompson et al., Cell 56:313 [1989]); and electroporation of embryos (Lo, Mol Cell Biol 3:1803 [1983]).

The present invention provides for transgenic animals that carry a card-3 or card-4 transgene in all of their cells, as well as animals that carry a transgene in some, but not all of their cells. For example, the invention provides for mosaic animals. The card-3 or card-4 transgene can be integrated as a single transgene or in concatamers, for example, head-to-head tandems or head-to-tail tandems. The transgene can also be selectively introduced into, and activated in, a particular cell type (Lasko et al., Proc Natl Acad Sci USA 89:6232 [1992]). The regulatory sequences required for such a cell-type specific activation will depend upon the particular cell type of interest, and will be apparent to those of skill in the art.

When it is desired that a card-3 or card-4 transgene be integrated into the chromosomal site of an endogenous card-3 or card-4 gene, gene targeting is preferred. Briefly, when such a technique is to be used, vectors containing some nucleotide sequences homologous to an endogenous card-3 or card-4 gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous card-3 or card-4 gene in only that cell type (Gu et al., Science 265:103 [1984]). The regulatory sequences required for such a cell-type specific inactivation will depend upon the particular cell type of interest, and will be apparent to those of skill in the art. These techniques are useful for preparing "knock outs" having no functional card-3 or card-4 gene.

Once transgenic animals have been generated, the expression of the recombinant card-3 or card-4 gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of card-3 or card-4 gene-expressing tissue can also be evaluated immunocytochemically using antibodies specific for the CARD-3 or CARD-4 transgene product.

For a review of techniques that can be used to generate and assess transgenic animals, those of ordinary skill in the art can consult Gordon (Intl Rev Cytol 115:171 [1989]), and may obtain additional guidance from, for example: Hogan et al., Manipulating the Mouse Embryo, Cold Spring Harbor Press, Cold Spring Harbor, N.Y. (1986); Krimpenfort et al., Bio/Technology 9:86 (1991); Palmiter et al., Cell 41:343 (1985); Kraemer et al., Genetic Manipulation of the Early Mammalian Embryo, Cold Spring Harbor Press, Cold Spring Harbor, N.Y. (1985); Hammer et al., Nature 315:680 (1985); Purcel et al., Science 244:1281 (1986); and U.S. Pat. Nos. 5,175,385 and 5,175,384.

The transgenic animals of the invention can be used to determine the consequence of altering the expression of card-3 or card-4 in the context of various disease states. For example, card-3 or card-4 knock out mice can be generated using an established line of mice that serve as a model for a disease in which activity of the missing gene is impaired.

IV. Anti-CARD-3 and Anti-CARD-4 Antibodies

CARD-3 or CARD-4 polypeptides (or immunogenic fragments or analogs thereof) can be used to raise antibodies useful in the invention; such polypeptides can be produced by recombinant techniques or synthesized (see, for example, Solid Phase Peptide Synthesis, supra and Ausubel et al., supra). In general, CARD-3 or CARD-4 polypeptides can be coupled to a carrier protein, such as KLH, as described in Ausubel et al., supra, mixed with an adjuvant, and injected into a host mammal. Antibodies produced in that animal can then be purified by peptide antigen affinity chromatography.

In particular, various host animals can be immunized by injection with a CARD-3 or CARD-4 polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and Corynebacterium parvum. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')2 fragments, and molecules produced using a Fab expression library.

Monoclonal antibodies, which are homogeneous populations of antibodies to a particular antigen, can be prepared using the CARD-3 or CARD-4 polypeptides described above and standard hybridoma technology (see, for example, Kohler et al., Nature 256:495 [1975]; Kohler et al., Eur J Immunol 6:511 [1976]; Kohler et al., Eur J Immunol 6:292 [1976]; Hammerling et al., Monoclonal Antibodies and T Cell Hybridomas, Elsevier, N.Y. [1981]; Ausubel et al., supra).

In particular, monoclonal antibodies can be obtained by any technique that provides for the production of antibody molecules by continuous cell lines in culture such as described in Kohler et al., Nature 256:495 (1975), and U.S. Pat. No. 4,376,110; the human B-cell hybridoma technique (Kosbor et al., Immunology Today 4:72 [1983]; Cole et al., Proc Natl Acad Sci USA 80:2026 [1983]), and the EBV-hybridoma technique (Cole et al., Monoclonal Antibodies and Cancer Therapy, Alan R. Liss, Inc., pp. 77–96 [1983]). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific CARD-3 or CARD-4 recognition by Western blot or immunoprecipitation analysis by standard methods, for example, as described in Ausubel et al., supra. Antibodies that specifically recognize and bind to CARD-3 or CARD-4 are useful in the invention. For example, such antibodies can be used in an immunoassay to monitor the level of CARD-3 or CARD-4 produced by a mammal (e.g., to determine the amount or subcellular location of CARD-3 or CARD-4).

There are two major classes of antibodies which are within the scope of the present invention. The first class are antibodies that selectively bind to CARD-3 or CARD-4 polypeptide and not bind to other members of the caspase recruitment domain family of proteins. The second class are antibodies that bind to more than one member of the caspase recruitment domain family of proteins.

Preferably, CARD-3 or CARD-4 selective antibodies of the invention are produced using fragments of the CARD-3 or CARD-4 polypeptide that lie outside highly conserved regions and appear likely to be antigenic, by criteria such as high frequency of charged residues. Cross-reactive anti-CARD-3 or CARD-4 antibodies are produced using a fragment of CARD-3 or CARD-4 (e.g., the CARD) that is conserved amongst members of this family of proteins. In one specific example, such fragments are generated by standard techniques of PCR, and are then cloned into the pGEX expression vector (Ausubel et al., supra). Fusion proteins are expressed in E. coli and purified using a glutathione agarose affinity matrix as described in Ausubel et al., supra.

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections.

Antiserum is also checked for its ability to immunoprecipitate recombinant CARD-3 or CARD-4 polypeptides or control proteins, such as glucocorticoid receptor, CAT, or luciferase.

The antibodies can be used, for example, in the detection of CARD-3 or CARD-4 in a biological sample as part of a diagnostic assay or to reduce CARD-3 or CARD-4 activity as part of a therapeutic regime (e.g., to reduce an undesirable level of CARD-3 or CARD-4 activity). Antibodies also can be used in a screening assay to measure the effect of a candidate compound on expression or localization of CARD-3 or CARD-4. Additionally, such antibodies can be used in conjunction with the gene therapy techniques. For example, they may be used to evaluate the normal and/or engineered card-3 or card-4-expressing cells prior to their introduction into the patient.

In addition, techniques developed for the production of "chimeric antibodies" (Morrison et al., Proc Natl Acad Sci USA 81:6851 [1984]; Neuberger et al., Nature 312:604 [1984]; Takeda et al., Nature 314:452 [1984]) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against a CARD-3 or CARD-4 polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed (Huse et al., Science 246:1275 [1989]) to allow rapid and easy identification of monoclonal Fab fragments with the desired specificity.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics 7:13 [1994]; and U.S. Pat. Nos. 5,545,806 and 5,569,825).

The methods described herein, in which anti☐CARD-3 or CARD-4 antibodies are employed, can be performed, for example, by utilizing pre-packaged diagnostic kits comprising at least one specific antibody reagent described herein, which may be conveniently used, for example, in clinical settings, to diagnose patients exhibiting symptoms of the disorders associated with aberrant expression of card-3 or card-4.

V. Antisense Nucleic Acid Molecules

Treatment regimes based on an "antisense" approach involve the design of oligonucleotides (either DNA or RNA) that are complementary to a portion of a selected mRNA. These oligonucleotides bind to complementary mRNA transcripts and prevent their translation. Absolute complementarity, although preferred, is not required. A sequence "complementary" to a portion of an RNA molecule, as referred to herein, is a sequence having sufficient complementarily to hybridize with the RNA, forming a stable duplex; in the case of double-stranded antisense nucleic acids, a single strand of the duplex DNA can be tested, or triplex formation can be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One of ordinary skill in the art can ascertain a tolerable degree of mismatch by use of standard procedures to determine the melting point of the hybridized complex.

Oligonucleotides that are complementary to the 5' end of the message, for example, the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, Nature 372:333 [1984]). Thus, oligonucleotides complementary to either the 5' or 3' non-translated, non-coding regions of a CARD-3 or CARD-4 gene, could be used in an antisense approach to inhibit translation of endogenous CARD-3 or CARD-4 mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of card-3 or card-4 mRNA, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

Regardless of the choice of target sequence, as with other therapeutic strategies directed to card-3 or card-4, it is preferred that in vitro studies are first performed to assess the ability of an antisense oligonucleotide to inhibit gene expression. If desired, the assessment can be quantitative. It is preferred that these studies utilize controls that distinguish between antisense gene inhibition and any nonspecific biological effect that an oligonucleotide may cause. It is also preferred that these studies compare levels of the target RNA or protein with that of an internal control RNA or protein. Additionally, it is envisioned that results obtained using an antisense oligonucleotide are compared with those obtained using a control oligonucleotide. Preferably, the control oligonucleotide is of approximately the same length as the test oligonucleotide, and the nucleotide sequence of the control oligonucleotide differs from that of the test antisense sequence no more than is necessary to prevent specific hybridization between the control oligonucleotide and the targeted RNA sequence.

The oligonucleotides can contain DNA or RNA, or they can contain chimeric mixtures, derivatives, or modified versions thereof that are either single-stranded or double-stranded. The oligonucleotide can be modified at the base moiety, sugar moiety, or phosphate backbone, for example, to improve stability of the molecule, hybridization, etc. Modified sugar moieties can be selected from the group including, but not limited to, arabinose, 2-fluoroarabinose, xylulose, and hexose. A modified phosphate backbone can be selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The oligonucleotide can include other appended groups such as peptides (e.g., for disrupting the transport properties of the molecule in host cells in vivo), or agents that facilitate transport across the cell membrane (as described, for example, in Letsinger et al., Proc Natl Acad. Sci USA 86:6553 [1989]; Lemaitre et al., Proc Natl Acad Sci USA 84:648 [1987]; PCT Publication No. WO 88/09810) or the blood-brain barrier (see, for example, PCT Publication No. WO 89/10134), or hybridization-triggered cleavage agents (see, for example, Krol et al., BioTechniques 6:958 [1988]), or intercalating agents (see, for example, Zon, Pharm Res 5:539 [1988]). To this end, the oligonucleotide can be conjugated to another molecule, for example, a peptide, a hybridization triggered cross-linking agent, a transport agent, or a hybridization-triggered cleavage agent.

An antisense oligonucleotide of the invention can comprise at least one modified base moiety that is selected from the group including, but not limited to, 5-fluoro-uracil, 5-bromouracil, 5-chlorouracil, 5-iodouracil, hypoxanthine, xantine, 4-acetylcytosine, 5-(carboxyhydroxyl-methyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thio-uracil, 5-methyluracil, uracil-5-oxyacetic acid methylester, uracil-5-oxyacetic acid (v), 5-methyl-2-thiouracil, 2-(3-amino-3-N-2-carboxypropyl) uracil, (acp3)w, and 2,6-diaminopurine.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl Acids Res 15:6625 [1987]). The oligonucleotide is a 2'-0-methylribonucleotide (Inoue et al., Nucl Acids Res 15:6131 [1987]), or a chimeric RNA-DNA analog (Inoue et al., FEBS Lett 215:327 [1987]).

Antisense oligonucleotides of the invention can be synthesized by standard methods known in the art, for example, by use of an automated DNA synthesizer (such as are commercially available from Biosearch, Applied Biosystems, etc.). As examples, phosphorothioate oligonucleotides can be synthesized by the method of Stein et al. (Nucl Acids Res 16:3209 [1988]), and methylphosphonate oligonucleotides can be prepared by use of controlled pore glass polymer supports (Sarin et al., Proc Natl Acad Sci USA 85:7448 [1988]).

For therapeutic application, antisense molecules of the invention should be delivered to cells that express card-3 or card-4 in vivo. A number of methods have been developed for delivering antisense DNA or RNA to cells; for example, antisense molecules can be injected directly into the tissue site. Alternatively, modified antisense molecules, which are designed to target cells that express card-3 or card-4 (e.g., antisense molecules linked to peptides or antibodies that specifically bind receptors or antigens expressed on the target cell surface) can be administered systemically.

However, it is often difficult to achieve intracellular concentrations of antisense molecules that are sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with endogenous card-3 or card-4 transcripts and thereby prevent translation of card-3 or card-4 mRNA. For example, a vector can be introduced in vivo in such a way that it is taken up by a cell and thereafter directs the transcription of an antisense RNA. Such a vector can remain episomal or become chromosomally integrated, as long as it can be transcribed to produce the desired antisense RNA.

Vectors encoding a card-3 or card-4 antisense sequence can be constructed by recombinant DNA technology methods that are standard practice in the art. Suitable vectors include plasmid vectors, viral vectors, or other types of vectors known or newly discovered in the art. The criterion for use is only that the vector be capable of replicating and expressing the card-3 or card-4 antisense molecule in mammalian cells. Expression of the sequence encoding the antisense RNA can be directed by any promoter known in the art to act in mammalian, and preferably in human, cells. Such promoters can be inducible or constitutively active and include, but are not limited to: the SV40 early promoter region (Bemoist et al., Nature 290:304 [1981]); the promoter contained in the 3' long terminal repeat of Rous sarcoma virus (Yamamoto et al., Cell 22:787 [1988]); the herpes thymidine kinase promoter (Wagner et al., Proc Natl Acad Sci USA 78:1441 [1981]); or the regulatory sequences of the metallothionein gene (Brinster et al., Nature 296:39 [1988]).

VI. Ribozymes

Ribozyme molecules designed to catalytically cleave card-3 or card-4 mRNA transcripts also can be used to prevent translation of card-3 or card-4 mRNA and expression of CARD-3 or CARD-4 polypeptides (see, for example, PCT Publication WO 90/11364; Saraver et al., Science 247:1222 [1990]). While various ribozymes that cleave mRNA at site-specific recognition sequences can be used to destroy card-3 or card-4 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'□UG□3'. The construction and production of hammerhead ribozymes is well known in the art (Haseloff et al., Nature 334:585 [1988]). There are numerous examples of potential hammerhead ribozyme cleavage sites within the nucleotide sequence of human card-3 and card-4 cDNA. Preferably, the ribozyme is engineered so that the cleavage recognition site is located near the 5' end of the CARD-3 or CARD-4 mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., Science 224:574 [1984]; Zaug et al., Science 231:470 [1986]; Zug et al., Nature 324:429 [1986]; PCT Application No. WO 88/04300; and Been et al., Cell 47:207 [1986]). The Cech-type ribozymes have an eight base☐pair sequence that hybridizes to a target RNA sequence, whereafter cleavage of the target RNA takes place. The invention encompasses those Cech-type ribozymes that target eight base-pair active site sequences present in CARD-3 or CARD-4.

As in the antisense approach, the ribozymes can be composed of modified oligonucleotides (e.g., for improved stability, targeting, etc.), and should be delivered to cells which express the card-3 or card-4 in vivo. A preferred method of delivery involves using a DNA construct "encoding" the ribozyme under the control of a strong constitutive pol III or pol II promoter, so that transfected cells will produce sufficient quantities of the ribozyme to destroy endogenous card-3 or card-4 messages and inhibit translation. Because ribozymes, unlike antisense molecules, are catalytic, a lower intracellular concentration is required for efficiency.

VII. Peptide Nucleic Acids

Nucleic acid molecules encoding CARD-3 or CARD-4 (or a fragment thereof) can be modified at the base moiety, sugar moiety, or phosphate backbone to improve, for example, the stability or solubility of the molecule or its ability to hybridize with other nucleic acid molecules. For example, the deoxyribose phosphate backbone of the nucleic acid can be modified to generate peptide nucleic acids, as described in Hyrup et al., Bioorganic Med Chem 4:5 (1996). As used herein, the terms "peptide nucleic acids" or "PNAs" refer to nucleic acid mimics, for example, DNA mimics, in which the deoxyribose phosphate backbone is replaced by a pseudopeptide backbone and only the four natural nucleotides are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., supra, and Perry-O'Keefe et al. Proc Natl Acad Sci USA 93:14670 (1996).

PNAs of card-3 or card-4 can be used in therapeutic and diagnostic applications. For example, PNAs can be used as antisense agents for sequence-specific modulation of gene expression by, for example, inducing transcription or translation arrest or inhibiting replication. PNAs of card-3 or card-4 can also be used, for example, in the analysis of single base pair mutations in a gene by, for example, PNA-directed PCR clamping; as artificial restriction enzymes when used in combination with other enzymes, for example, S1 nucleases (Hyrup et al., supra); or as probes or primers for DNA sequence and hybridization (Hyrup et al., supra, and Perry-O'Keefe, supra).

In other embodiments, PNAs of card-3 or card-4 can be modified, for example, to enhance their stability or cellular uptake, by attaching lipophilic or other helper groups to the PNA, by the formation of PNA-DNA chimeras, or by the use of liposomes or other techniques of drug delivery known in the art. For example, PNA-DNA chimeras of card-3 or card-4 can be generated that may combine the advantageous properties of PNA and DNA. Such chimeras allow DNA recognition enzymes, for example, RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleotides, and orientation (Hyrup et al., supra). The synthesis of PNA-DNA chimeras can be performed as described in Hyrup, supra, and Finn et al., Nucl Acids Res 24:3357 (1996). For example, a DNA chain can be synthesized on a solid support using standard phosphoramidite coupling chemistry and modified nucleoside analogs, e.g., 5'☐(4-methoxytrityl)amino-5'-deoxythymidine phosphoramidite, can be used between the PNA and the 5' end of DNA (Mag et al., Nucl Acids Res 17:5973 [1989]). PNA monomers are then coupled in a stepwise manner to produce a chimeric molecule with a 5' PNA segment and a 3' DNA segment (Finn et al., supra). Alternatively, chimeric molecules can be synthesized with a 5' DNA segment and a 3' PNA segment (Peterser et al., Bioorganic Med Chem Lett 5:1119 [1975]).

In other embodiments, the oligonucleotide may include other appended groups such as peptides (e.g., for targeting host cell receptors in vivo), or agents facilitating transport across the cell membrane (see, e.g., Letsinger et al., Proc Natl Acad Sci USA 86:6553 [1989]; Lemaitre et al., Proc Natl Acad Sci USA 84:648 [1987], and PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., BioTech 6:958 [1988]) or integrating agents (see, e.g., Zon, Pharm Res 5:539 [1988]). To this end, the oligonucleotide may be conjugated to another molecule, for example, a peptide, hybridization triggered cross-linking agent, transport agent, hybridization-triggered cleavage agent etc.

VIII. Proteins that Associate with CARD-3 or CARD-4

The invention also features methods for identifying polypeptides that can associate with CARD-3 or CARD-4, as well as the isolated interacting protein. Any method that is suitable for detecting protein-protein interactions can be employed to detect polypeptides that associate with CARD-3 or CARD-4, whether these polypeptides associate with the transmembrane, intracellular, or extracellular domains of CARD-3 or CARD-4. Among the traditional methods that can be employed are co☐immunoprecipitation, crosslinking, and co☐purification through gradients or chromatographic columns of cell lysates or proteins obtained from cell lysates and the use of CARD-3 or CARD-4 to identify proteins in the lysate that interact with CARD-3 or CARD-4. For these assays, the CARD-3 or CARD-4 polypeptide can be a full length CARD-3 or CARD-4, an extracellular domain of CARD-3 or CARD-4, or some other suitable CARD-3 or CARD-4 polypeptide. Once isolated, such an interacting protein can be identified and cloned and then used, in conjunction with standard techniques, to alter the activity of the CARD-3 or CARD-4 polypeptide with which it interacts. For example, at least a portion of the amino acid sequence of a protein that interacts with CARD-3 or CARD-4 can be ascertained using techniques well known to those of skill in the art, such as via the Edman degradation technique. The amino acid sequence obtained can be used as a guide for the generation of oligonucleotide mixtures that can be used to screen for gene sequences encoding the interacting protein. Screening can be accomplished, for example, by standard hybridization or PCR techniques. Techniques for the generation of oligonucleotide mixtures and the screening are well-known (Ausubel, supra; and "PCR Protocols: A Guide to Methods and Applications," Innis et al., eds. Academic Press, Inc., NY, 1990).

Additionally, methods can be employed that result directly in the identification of genes that encode proteins that interact with CARD-3 or CARD-4. These methods include, for example, screening expression libraries, in a manner similar to the well known technique of antibody probing of λgt11 libraries, using labeled CARD-3 or CARD-4 polypeptide or a CARD-3 or CARD-4 fusion protein, for example, a CARD-3 or CARD-4 polypeptide or domain fused to a marker such as an enzyme, fluorescent dye, a luminescent protein, or to an IgFc domain.

There are also methods available that can detect protein-protein interaction in vivo. A method which detects protein interactions in vivo is the two-hybrid system (Chien et al., Proc Natl Acad Sci USA 88:9578 [1991]). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding CARD-3 or CARD-4, a CARD-3 or CARD-4 polypeptide, or a CARD-3 or CARD-4 fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or LacZ) whose regulatory region contains the transcription activator's binding site. Either hybrid protein alone cannot activate transcription of the reporter gene: the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, CARD-3 or CARD-4 may be used as the bait gene product. Total genomic or cDNA sequences are fused to the DNA encoding an activation domain. This library and a plasmid encoding a hybrid of bait CARD-3 or CARD-4 gene product fused to the DNA-binding domain are co-transformed into a yeast reporter strain, and the resulting transformants are screened for those that express the reporter gene. For example, a bait card-3 or card-4 gene sequence, such as that encoding CARD-3 or CARD-4 or a domain of CARD-3 or CARD-4 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait CARD-3 or CARD-4 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait card-3 or card-4 gene-GAL4 fusion plasmid into a yeast strain which contains a lacZ gene driven by a promoter which contains GAL4 activation sequence. A cDNA encoded protein, fused to GAL4 transcriptional activation domain, that interacts with bait CARD-3 or CARD-4 gene product will reconstitute an active GAL4 protein and thereby drive expression of the HIS3 gene. Colonies that express HIS3 can then be purified from these strains and used to produce and isolate the bait CARD-3 or CARD-4-interacting protein using techniques routinely practiced in the art.

IX. Detection of CARD-3 or CARD-4 and Nucleic Acid Molecules Encoding CARD-3 or CARD-4 and Related Diagnostic Assays The invention encompasses methods for detecting the presence of card-3 or card-4 protein or nucleic acid in a biological sample as well as methods for measuring the level of card-3 or card-4 protein or nucleic acid in a biological sample. Such methods are useful for diagnosis of disorders associated with aberrant expression of card-3 or card-4.

An exemplary method for detecting the presence or absence of card-3 or card-4 in a biological sample involves obtaining a biological sample from a test subject and contacting the biological sample with a compound or an agent capable of detecting a CARD-3 or CARD-4 polypeptide or a card-3 or card-4 nucleic acid (e.g., mRNA or genomic DNA). A preferred agent for detecting card-3 or card-4 mRNA or genomic DNA is a labeled nucleic acid probe capable of hybridizing to card-3 or card-4 mRNA or genomic DNA. The nucleic acid probe can be, for example, a full-length card-3 or card-4 nucleic acid molecule, such as a nucleic acid molecule having the sequence of SEQ ID NO:2 or SEQ ID NO:4, or a portion thereof, such as an oligonucleotide of at least 15, 30, 50, 100, 250, or 500 nucleotides in length and sufficient to specifically hybridize under stringent conditions to card-3 or card-4 mRNA or genomic DNA.

A preferred agent for detecting a CARD-3 or CARD-4 polypeptide is an antibody capable of binding to an CARD-3 or CARD-4 polypeptide, preferably an antibody with a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells and fluids present within a subject. That is, the detection method of the invention can be used to detect card-3 or card-4 mRNA, a CARD-3 or CARD-4 polypeptide, or card-3 or card-4 genomic DNA in a biological sample in vitro as well as in vivo. For example, in vitro techniques for detection of card-3 or card-4 mRNA include Northern hybridizations and in situ hybridizations. In vitro techniques for detection of a CARD-3 or CARD-4 polypeptide include enzyme linked immunosorbent assays (ELISAs), Western blots, immunoprecipitations and immunofluorescence. In vitro techniques for detection of card-3 or card-4 genomic DNA include Southern hybridizations. Furthermore, in vivo techniques for detection of a CARD-3 or CARD-4 polypeptide include introducing into a subject a labeled anti-CARD-3 or anti-CARD-4 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting a CARD-3 or CARD-4 polypeptide, card-3 or card-4 mRNA, or card-3 or card-4 genomic DNA, such that the presence of a CARD-3 or CARD-4 polypeptide, card-3 or card-4 mRNA, or card-3 or card-4 genomic DNA is detected in the biological sample, and comparing the presence of CARD-3 or CARD-4 polypeptide or card-3 or card-4 mRNA, or genomic DNA in the control sample with the presence of card-3 or card-4 polypeptides, mRNA or genomic DNA in a test sample.

The invention also encompasses kits for detecting the presence of card-3 or card-4 nucleic acid molecules or CARD-3 or CARD-4 polypeptides in a biological sample. For example, the kit can contain a labeled compound or agent capable of detecting a CARD-3 or CARD-4 polypeptide or a card-3 or card-4 mRNA molecule in a biological sample; means for determining the amount of card-3 or card-4 protein or nucleic acid in the sample; and means for comparing the amount of card-3 or card-4 protein or nucleic acid in the sample with a standard. The compound or agent can be packaged in a suitable container. The kit can further contain instructions for using the kit to detect a CARD-3 or CARD-4 polypeptide or card-3 or card-4 nucleic acid molecule.

X. Prognostic Assays

The invention also encompasses prognostic assays that can be used to identify subjects having or at risk of developing a or disorder associated with aberrant card-3 or card-4 expression or CARD-3 or CARD-4 activity. Thus, the present invention includes methods in which a test sample is obtained from a subject and the level, or presence, or allelic form of card-3 or card-4 nucleic acid molecules or CARD-3 or CARD-4 polypeptides is assessed. As used herein, a "test sample" refers to a biological sample obtained from a subject of interest. For example, a test sample can be a biological fluid (e.g., serum), a cell sample, or tissue.

The prognostic assays described herein can be used to indicate the best therapeutic regimen (e.g., by administering an agonist, antagonist, peptidomimetic, polypeptide, nucleic acid, small molecule or other drug candidate) to treat a disease or disorder associated with aberrant card-3 or card-4 expression or CARD-3 or CARD-4 activity.

The methods of the invention can also be used to detect genetic alterations in card-3 or card-4. The methods include detecting in a sample the presence or absence of a genetic alteration affecting the activity of a CARD-3 or CARD-4 polypeptide or the expression of a card-3 or card-4 gene. For example, such genetic alterations can be detected by ascertaining the existence of at least one of: (1) a deletion of one or more nucleotides from a card-3 or card-4 gene; (2) an addition of one or more nucleotides to a card-3 or card-4 gene; (3) a substitution of one or more nucleotides of a card-3 or card-4 gene; (4) a chromosomal rearrangement of a card-3 or card-4 gene; (5) an alteration in the level of a messenger RNA transcript of a card-3 or card-4 gene; (6) aberrant modification of a card-3 or card-4 gene such as DNA methylation; and (7) an altered post☐translational modification of a CARD-3 or CARD-4 polypeptide.

In certain embodiments, detection of the alteration involves the use of a probe/primer in a polymerase chain reaction (PCR; see, e.g., U.S. Pat. Nos. 4,683,195 and 4,683,202), such as anchor PCR or RACE PCR, or alternatively, in a ligation chain reaction (LCR; see, e.g., Landegran et al., Science 241:1077 [1988]; and Nakazawa et al. Proc Natl Acad Sci USA 91:360 [1994]), the latter of which can be particularly useful for detecting point mutations in the card-3 or card-4 gene (see Abavaya et al., Nucl Acids Res 23:675 [1995]). This method can include the steps of collecting a sample of cells from a patient, isolating nucleic acid (e.g., genomic DNA, mRNA, or both) from the cells of the sample, contacting the nucleic acid sample with one or more primers which specifically hybridize to a card-3 or card-4 gene under conditions such that hybridization and amplification of the card-3 or card-4 nucleic acid (if present) occurs, and detecting the presence or absence of an amplification product, or detecting the size of the amplification product and comparing the length of the amplification product to that of the amplification product from a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., Proc Natl Acad Sci USA 87:1874 [1990]), transcriptional amplification system (Kwoh et al., Proc Natl Acad Sci USA 86:1173 [1989]), Q-Beta Replicase (Lizardi et al., Bio/Technology 6:1197 [1988]), or any other nucleic acid amplification method, followed by the detection of the amplified molecules using techniques well known to those of ordinary skill in the art. These detection schemes are especially useful for the detection of nucleic acid molecules if such molecules are present in very low number.

In an alternative embodiment, alterations in a CARD-3 or CARD-4 gene from a sample cell can be identified by identifying changes in a restriction enzyme cleavage pattern. For example, sample and control DNA is isolated, optionally amplified, and digested with one or more restriction endonucleases. Fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, alterations in card-3 or card-4 can be identified by hybridizing sample and control nucleic acids, e.g., DNA or RNA, to high density arrays containing tens to thousands of oligonucleotide probes (Cronin et al., Human Mutation 7:244 [1996]); Kozal et al., Nature Medicine 2:753 [1996]). For example, alterations in CARD-3 or CARD-4 can be identified in two dimensional arrays containing light-generating DNA probes as described in Cronin et al., supra. Briefly, a hybridization array of sequential, overlapping probes can be used to scan through long stretches of DNA to identify base changes between the sample and control sequences, allowing the identification of point mutations. This step is followed by a hybridization to an array that further characterizes specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the card-3 or card-4 gene and detect mutations by comparing the sequence of the sample card-3 or card-4 with the corresponding wild-type (control) sequence. Examples of sequencing reactions include those based on techniques developed by Maxim and Gilbert (Proc Natl Acad Sci USA 74:560 [1977]) or Sanger (Proc Natl Acad Sci USA 74:5463 [1977]). It is also contemplated that any of a variety of automated sequencing procedures can be utilized when performing the diagnostic assays (Bio/Techniques 19:448 [1995]) including sequencing by mass spectrometry (see, e.g. PCT International Publication No. WO 94/16101; Cohen et al. Adv. Chromatogr. 36:127 [1996]; and Griffin et al., Appl Biochem Biotechnol 38:147 [1993]).

Other methods of detecting mutations in the card-3 or card-4 gene include methods in which protection from cleavage agents is used to detect mismatched bases in RNA/RNA or RNA/DNA duplexes (Myers et al. Science 230:1242 [1985]). In general, heteroduplexes are formed by hybridizing (labeled) RNA or DNA containing the wild-type card-3 or card-4 is sequence with potentially mutant RNA or DNA obtained from a tissue sample. The double-stranded duplexes are treated with an agent which cleaves single-stranded regions of the duplex. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated on denaturing polyacrylamide gels to determine the site of mutation. (see, for example, Cotton et al., Proc Natl Acad Sci USA 85:4397 [1988]; Saleeba et al., Methods Enzymol 217:286 [1992]. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in card-3 or card-4 cDNAs. For example, the mutY enzyme of E. coli cleaves A at G/A mismatches (Hsu et al., Carcinogenesis 15:1657 [1994]). According to an exemplary embodiment, a probe based on a card-3 or card-4 sequence is hybridized to a cDNA or another nucleic acid representing a cDNA. The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify mutations in card-3 or card-4 genes. For example, single strand conformation polymorphism (SSCP) can be used to detect differences in electrophoretic mobility between mutant and wild type nucleic acids (Orita et al., Proc Natl Acad Sci USA 86:2766 and Cotton Mutat Res 285:125 [1993]; and Hayashi et al., Genet Anal Tech Appl 9:73 [1992]). Sample and control single-stranded card-3 or card-4 nucleic acids will be denatured and allowed to renature. The secondary structure of single-stranded nucleic acids varies according to sequence. The resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the method utilizes heteroduplex analysis to separate double stranded heteroduplex molecules on the basis of changes in electrophoretic mobility (Kee et al., Trends Genet 7:5 [1991]).

In yet another embodiment, the movement of mutant or wild-type fragments in a polyacrylamide gel containing a gradient of denaturant is assayed using denaturing gradient gel electrophoresis (DGGE; Myers et al., Nature 313:495 [1985]). When DGGE is used as the method of analysis, DNA will be modified to insure that it does not completely denture, for example by adding a GC clamp of approximately 40 bp. In a further embodiment, a temperature gradient is used in place of a denaturing gradient to identify differences in the mobility of control and sample DNA (Rosenbaum et al., Biophys Chem 265:12753 [1987]).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al., Nature 324:163 [1986]; Saiki et al., Proc Natl Acad Sci USA 86:6230 [1989]). Such allele specific oligonucleotides are hybridized to PCR amplified target DNA or oligonucleotides.

Alternatively, allele specific amplification technology which depends on selective PCR amplification may be used in conjunction with the instant invention. Oligonucleotides used as primers for specific amplification may carry the mutation of interest in the center of the molecule, so that amplification depends on differential hybridization (Gibbs et al., Nucl Acids Res 17:2437 [1989]) or at the extreme 3' end of one primer where, under appropriate conditions, mismatch can prevent, or reduce polymerase extension (Prossner, Tib/Tech 11:238 [1993]). In addition it may be desirable to introduce a novel restriction site near the mutation for endonuclease-based detection (Gasparini et al., Mol Cell Probes 6:1 [1992]). It is anticipated that in certain embodiments amplification may also be performed using Taq ligase for amplification (Barany, Proc Natl Acad Sci USA 88:89 [1991]). In such cases, ligation will occur only if there is a perfect match at the 3' end of the 5' sequence making it possible to detect the presence of a known mutation at a specific site by looking for the presence of absence of the amplification product.

The methods described herein may be performed, for example, by utilizing pre-packaged diagnostic kits comprising at least one probe nucleic acid or antibody reagent described herein, which may be conveniently used, for example, in a clinical setting to diagnose patient exhibiting symptoms or a family history of a disease or disorder involving abnormal card-3 or card-4 activity.

XI. Pharmacogenetics

Agents or modulators which have a stimulatory or inhibitory effect on card-3 or card-4 gene expression can be administered to individuals for prophylactic or therapeutic treatment of disorders associated with aberrant card-3 or card-4 activity. The pharmacogenetics (i.e., the study of the relationship between an individual's genotype and that individual's response to a foreign compound or drug) of the individual permits the selection of effective agents and can further be used to determine appropriate dosages and therapeutic regimens. Accordingly, the activity of CARD-3 or CARD-4 polypeptides or expression of card-3 or card-4 nucleic acids can be determined and used to select an appropriate agent for therapeutic or prophylactic treatment of the individual.

XII. Monitoring in Clinical Trials

Monitoring the influence of agents (e.g., drugs, compounds) on the expression of card-3 or card-4 or the activity of CARD-3 or CARD-4 can be applied in clinical trials. For example, the effectiveness of an agent determined by a screening assay as described herein to increase or decrease card-3 or card-4 gene expression or increase or decrease CARD-3 or CARD-4 activity, can be monitored in subjects exhibiting increased or decreased card-3 or card-4 gene expression or increased or decreased CARD-3 or CARD-4 activity.

XIII. Screening Assays for Compounds that Modulate CARD-3 or CARD-4 Expression or Activity The invention also encompasses methods for identifying compounds that interact with CARD-3 or CARD-4 (or a domain of CARD-3 or CARD-4) including, but not limited to, compounds that interfere with the interaction of CARD-3 or CARD-4 with transmembrane, extracellular, or intracellular proteins which regulate CARD-3 or CARD-4 activity and compounds which modulate CARD-3 or CARD-4 activity. Also encompasses are method for identifying compounds which bind to card-3 or card-4 gene regulatory sequences (e.g., promoter sequences) and which may modulate card-3 or card-4 gene expression.

The compounds which may be screened in accordance with the invention include, but are not limited to peptides, antibodies and fragments thereof, and other organic compounds that bind to CARD-3 or CARD-4 and increase or decrease activity.

Such compounds may include, but are not limited to, peptides such as, for example, soluble peptides, including but not limited to members of random peptide libraries; (Lam et al., Nature 354:82 [1991]; Houghten et al., Nature 354:84 [1991]), and combinatorial chemistry-derived molecular library made of D- and/or L configuration amino acids, phosphopeptides (including, but not limited to, members of random or partially degenerate, directed phosphopeptide libraries; Songyang et al., Cell 72:767 [1993]), antibodies (including, but not limited to, polyclonal, monoclonal, humanized, anti-idiotypic, chimeric or single chain antibodies, and FAb, F(abN)2 and FAb expression library fragments, and epitope-binding fragments thereof), and small organic or inorganic molecules.

Other compounds which can be screened in accordance with the invention include but are not limited to small organic molecules that are able to gain entry into an appropriate cell and affect the expression of the card-3 or card-4 gene or activity of CARD-3 or CARD-4 protein.

Computer modelling and searching technologies permit identification of compounds, or the improvement of already identified compounds, that can modulate card-3 or card-4 expression or activity. Having identified such a compound or composition, the active sites or regions are identified. Such active sites might typically be a binding for a natural modulator of activity. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the modulator (or ligand) is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed modulator (ligand), natural or artificial, which may increase the accuracy of the active site structure determined.

If an incomplete or insufficiently accurate structure is determined, the methods of computer-based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential CARD-3 or CARD-4 modulating compounds.

Alternatively, these methods can be used to identify improved modulating compounds from a previously identified modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen et al., Acta Pharmaceutical Fennica 97:159 [1993]; Ripka, New Scientist 54–57 [Jun. 16, 1988]; McKinaly and Rossmann, Annu Rev Pharmacol Toxicol 29:111 [1989]; Perry and Davies, OSAR: Quantitative Structure-Activity Relationships in Drug Design, pp. 189–193 (Alan R. Liss, Inc. 1989); Lewis and Dean, Proc R Soc Lond 236:125 [1989]; and 141 [1980]; and, with respect to a model receptor for nucleic acid components, Askew et al., J Am Chem Soc 111:1082 [1989]). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators of CARD-3 or CARD-4 activity Compounds identified via assays such as those described herein may be useful, for example, in elaborating the biological function of CARD-3 or CARD-4 and for the treatment of disorders associated with aberrant card-3 or card-4 activity or expression. Assays for testing the effectiveness of compounds identified with the above-described techniques are discussed below.

In vitro systems may be designed to identify compounds capable of interacting with CARD-3 or CARD-4 (or a domain of CARD-3 or CARD-4). Compounds identified may be useful, for example, in modulating the activity of wild type and/or mutant CARD-3 or CARD-4; may be useful in elaborating the biological function CARD-3 or CARD-4; may be utilized in screens for identifying compounds that disrupt normal CARD-3 or CARD-4 interactions; or may in themselves disrupt such interactions.

The principle of the assays used to identify compounds that bind to CARD-3 or CARD-4 involves preparing a reaction mixture of CARD-3 or CARD-4 (or a domain thereof) and the test compound under conditions and for a time sufficient to allow the two components to interact and bind, thus forming a complex which can be removed and/or detected in the reaction mixture. The CARD-3 or CARD-4 species used can vary depending upon the goal of the screening assay. In some situations it is preferable to employ a peptide corresponding to a domain of CARD-3 or CARD-4 fused to a heterologous protein or polypeptide that affords advantages in the assay system (e.g., labeling, isolation of the resulting complex, etc.) can be utilized.

The screening assays can be conducted in a variety of ways. For example, one method to conduct such an assay involves anchoring CARD-3 or CARD-4 protein, polypeptide, peptide or fusion protein or the test substance onto a solid phase and detecting CARD-3 or CARD-4/test compound complexes anchored on the solid phase at the end of the reaction. In one embodiment of such a method, the CARD-3 or CARD-4 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for CARD-3 or CARD-4 protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with CARD-3 or CARD-4. To this end, cell lines that express card-3 or card-4, or cell lines that have been genetically engineered to express card-3 or card-4 can be used.

XIV. Assays for Compounds that Interfere with the Interaction Between CARD-3 or CARD-4 and a Protein Binding Partner Proteins that interact with the CARD-3 or CARD-4 are referred to, for purposes of this discussion, as "binding partners". Such binding partners can be involved in regulating CARD-3 or CARD-4 activity. Therefore, it is desirable to identify compounds that interfere with or disrupt the interaction of such binding partners with CARD-3 or CARD-4. Such compounds may be useful in regulating the activity of the CARD-3 or CARD-4 and treating disorders associated with aberrant CARD-3 or CARD-4 activity.

The basic principle of the assay systems used to identify compounds that interfere with the interaction between the CARD-3 or CARD-4 and binding partner or partners involves preparing a reaction mixture containing CARD-3 or CARD-4 protein, polypeptide, peptide or fusion protein and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the CARD-3 or CARD-4 moiety and its binding partner. Control reaction mixtures are incubated without the test compound or with a non-active control compound. The formation of any complexes between the CARD-3 or CARD-4 moiety and the binding partner is then detected. The formation of a complex in the control reaction, but not in the reaction mixture containing the test compound, indicates that the compound interferes with the interaction of CARD-3 or CARD-4 and the interactive binding partner. Additionally, complex formation within reaction mixtures containing the test compound and normal CARD-3 or CARD-4 protein may also be compared to complex formation within reaction mixtures containing the test compound and a mutant CARD-3 or CARD-4. This comparison may be important in those cases wherein it is desirable to identify compounds that disrupt interactions of mutant but not normal CARD-3 or CARD-4.

The assay for compounds that interfere with the interaction of the CARD-3 or CARD-4 and a binding partner can be conducted in a heterogeneous or homogeneous format. Heterogeneous assays involve anchoring either the CARD-3 or CARD-4 protein, polypeptide, peptide, or fusion protein, or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to or simultaneously with the CARD-3 or CARD-4 moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the CARD-3 or CARD-4 moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of CARD-3 or CARD-4 (or a domain thereof) or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a directly or indirectly labeled antibody specific for the initially non-immobilized species. Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected, e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the CARD-3 or CARD-4 moiety and the interactive binding partner is prepared in which either the CARD-3 or CARD-4 or its binding partners is labeled, but the signal generated by the label is quenched due to formation of the complex (see, e.g., U.S. Pat. No. 4,109,496). The addition of a test substance that competes with and displaces one of the species from the preformed complex will result in the generation of a signal above background. Thus test substances which disrupt CARD-3 or CARD-4/intracellular binding partner interaction can be identified.

In a particular embodiment, a CARD-3 or CARD-4 fusion proteins can be prepared for immobilization. For example, the CARD-3 or CARD-4 or a peptide fragment thereof can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope 125I for example, by methods routinely practiced in the art. In a heterogeneous assay, the GST-CARD-3 or CARD-4 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between CARD-3 or CARD-4 and the interactive binding partner can be detected by measuring the amount of radioactivity that remains associated with the glutathione-agarose beads. A successful inhibition of the interaction by the test compound will result in a decrease in measured radioactivity.

Alternatively, the GST-CARD-3 or CARD-4 fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the CARD-3 or CARD-4/binding partner interaction can be detected by adding the labeled antibody and measuring the radioactivity associated with the beads.

In another embodiment of the invention, these same techniques can be employed using peptide fragments that correspond to the binding domains of CARD-3 or CARD-4 and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

XV. Methods for Reducing Card-3 or Card-4 Expression

Expression of card-3 or card-4 can be reduced through the use of modulatory compounds identified through the use of the screening methods described above. In addition, endogenous card-3 or card-4 gene expression can also be reduced by inactivating or "knocking out" the card-3 or card-4 gene or its promoter using targeted homologous recombination (see, for example, U.S. Pat. No. 5,464,764). For example, a mutant, non-functional card-3 or card-4 (or a completely unrelated DNA sequence) flanked by DNA homologous to the endogenous card-3 or card-4 gene (either the coding regions or regulatory regions of the card-3 or card-4 gene) can be used, with or without a selectable marker and/or a negative selectable marker, to transfect cells that express card-3 or card-4 in vivo. Insertion of the DNA construct, via targeted homologous recombination, results in inactivation of the card-3 or card-4 gene. Such approaches are particularly suited for use in developing animal models to study the role of card-3 or card-4; in this instance, modifications to ES (embryonic stem) cells can be used to generate animal offspring with an inactive card-3 or card-4 gene. However, a knock out approach can be adapted for use in humans, provided the recombinant DNA constructs are directly administered or targeted to the required site in vivo using appropriate viral vectors.

Alternatively, endogenous card-3 or card-4 gene expression can be reduced by targeting deoxyribonucleotide sequences complementary to the regulatory region of the card-3 or card-4 gene (i.e., the card-3 or card-4 promoter and/or enhancers) to form triple helical structures that prevent transcription of the card-3 or card-4 gene in target cells in the body (Helene, Anticancer Drug Res 6:569 [1981]; Helene et al., Ann NY Acad Sci 660:27 [1992]; and Maher, Bioassays 14:807 [1992]).

In addition, as discussed above, anti-sense molecules, ribozymes, and peptide nucleic acids can be used to reduce card-3 or card-4 expression.

XVI. Assays for the Identification of Compounds that Ameliorate Disorders Associated with Aberrant Card-3 or Card-4 Expression or Activity Compounds, including, but not limited to, compounds identified via assay techniques such as those described above may be useful for the treatment of disorders associated with aberrant card-3 or card-4 expression or aberrant CARD-3 or CARD-4 activity.

While animal model-based assays are particularly useful for the identification of such therapeutic compounds, cell-based assay systems are also very useful, particularly in combination with animal-model based assays. Such cell-based systems can include, for example, recombinant or non-recombinant cells which express card-3 or card-4. The effect of a selected modulatory compound on card-3 or card-4 expression can be measured using any of the above-described techniques for measuring CARD-3 or CARD-4 protein or card-3 or card-4 mRNA.

XVII. Effective Dose

Toxicity and therapeutic efficacy of the polypeptides of the invention and the compounds that modulate their expression or activity can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Polypeptides or other compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

XVIII. Formulations and Use

Pharmaceutical compositions for use in accordance with the present invention can be formulated in a conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Alternatively, the active ingredient can be in powder form for constitution with a suitable vehicle, for example, sterile pyrogen-free water, before use.

The compounds can also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (e.g., subcutaneously or intramuscularly) or by intramuscular injection. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The compositions can, if desired, be presented in a pack or dispenser device which may contain one or more unit dosage forms containing the active ingredient. The pack can, for example, comprise metal or plastic foil, such as a blister pack. The pack or dispenser device can be accompanied by instructions for administration.

The therapeutic compositions of the invention can also contain a carrier or excipient, many of which are known to persons of ordinary skill in the art. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol.

The nucleic acids, polypeptides, antibodies, or other modulatory compounds of the invention (i.e., compounds that alter the expression of card-3 or card-4 or the activity of CARD-3 or CARD-4) can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

XXI. Deposit Statement

The deposit clones describe above cultures have been deposited under conditions that assure that access to the cultures will be available during the pendency of the patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from a deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

A number of embodiments of the invention have been described. Nevertheless, it will be understood that various modifications may be made without departing from the spirit and scope of the invention.

What is claimed:

1. A method for determining whether a test compound alters the binding of CARD-3 to p75, comprising:
   a) measuring the binding of a first polypeptide a second polypeptide in the presence of a test compound, wherein the first polypeptide binds to p75 and comprises at least a CARD domain with at least 95% identity to the CARD domain of CARD-3 (amino acids 432–540 of SEQ ID NO:1), and wherein the second polypeptide comprises the death domain of p75; and
   b) determining that the test compound alters the binding of CARD-3 to p75 if the binding measured in step a) differs from the binding of the first polypeptide to the second polypeptide in the absence of the test compound.

2. A The method of claim 1, wherein the first polypeptide and the second polypeptide are in a cell.

3. The method of claim 2, wherein the cells is a neuronal cell.

4. The method of claim 2 wherein the cells is a Schwann cell.

5. The method of claim 1 wherein the first polypeptide comprises amino acids 432–540 of SEQ ID NO:1.

6. The method of claim 1 wherein the second polypeptide comprises full-length p75.

7. The method of claim 1 wherein the first polypeptide comprises SEQ ID NO:1.

8. The method of claim 1 wherein the second polypeptide comprises SEQ ID NO:13.

9. The method of claim 1 wherein the second polypeptide comprises SEQ ID NO:14.

10. The method of claim 2, wherein the cells expresses NGF.

11. A method for determining whether a test compound alters CARD-3 mediated NF-κB activity, comprising:
    a) measuring the effect of a test compound on NF-κB activity in a cell that expresses a polypeptide that activates NF-κB activity and comprises at least a CARD domain with at least 95% identity to the CARD domain of CARD-3 (amino acids 432–540 of SEQ ID NO:1) and at least a kinase domain with at least 95% identity to the kinase domain of CARD-3 (amino acids 1–300 of SEQ ID NO:1); and b) determining that the test compound alters CARD-3 mediated NP-κB activity when the effect measured in step a) is greater than the effect of the test compound on NP-κB activity in a cell that does not express the polypeptide.

12. The method of claim 11 wherein the cells are Schwann cells.

13. A method for determining whether a test compound inhibits the kinase activity of CARD-3, comprising:

a) measuring the phosphorylation of a CARD-3 substrate by a polypeptide in the absence of a test compound, wherein the polypeptide has protein kinase activity and comprises at least a kinase domain with at least 95% identity to the kinase domain of CARD-3 (amino acids 1–300 of SEQ ID NO:1); and b) determining that the teat compound inhibits the kinase activity of CARD-3 when the phosphorylation measured in step a) is more than the phosphorylation of a CARD-3 substrate by the polypeptide in the presence of the test compound.

14. A method for determining whether a test compound alters CARD-3 mediated apoptosis, comprising:

a) measuring the effect of a test compound on apoptosis of cells expressing a polypeptide that activates NE-κB activity and comprises at least a CARD domain with at least 95% identity to the CARD domain of CARD-3 (amino acids 432–540 of SEQ ID NO:1) and at least a kinase domain with at least 95% identity to the kinase domain of CARD-3 (amino acids 1–300 of SEQ ID NO:1);

b) determining that the test compound alters CARD-3 mediated apoptosis when the effect measured in step a) is greater than the effect of the test compound on apoptosis of cells that do not express the polypeptide.

15. The method of claim 14 wherein the cells are neuronal cells.

16. The method of claim 14 wherein the cells are Schwann cells.

17. The method of claim 1, wherein the first polypeptide comprises an amino acid sequence that is at least 95% identical to SEQ ID NO:1.

18. The method of claim 1, wherein the measuring of the binding of the first polypeptide to the second polypeptide is performed in vitro.

19. The method of claim 18, wherein the first and second polypeptides are polypeptides.

20. The method of claim 2, wherein the method is performed in the presence of NGF.

21. The method of claim 2, wherein the first polypeptide comprises amino acids 432–540 of SEQ ID NO:1.

22. The method of claim 2, wherein the first polypeptide comprises SEQ ID NO:1.

23. The method of claim 2, wherein the first polypeptide comprises an amino acid sequence that is at least 95% identical to SEQ ID NO:1.

24. The method of claim 2, wherein the second polypeptide comprises full-length p75.

25. The method of claim 2, wherein the second polypeptide comprises SEQ ID NO:13.

26. The method of claim 2, wherein the second polypeptide comprises SEQ ID NO:14.

27. The method of claim 11, wherein the method is performed in the presence of NGF.

28. The method of claim 11, wherein the cells are neuronal cells.

29. The method of claim 11, wherein the polypeptide comprises amino acids 1 to 300 and 432–540 of SEQ ID NO:1.

30. The method of claim 11, wherein the polypeptide comprises SEQ ID NO:1.

31. The method of claim 11, wherein the first polypeptide comprises an amino acid sequence that is at least 95% identical to SEQ ID NO:1.

32. The method of claim 11, wherein the cell expresses p75.

33. The method of claim 13, wherein the polypeptide comprises amino acids 1 to 300 of SEQ ID NO:1.

34. The method of claim 13, wherein the polypeptide comprises SEQ ID NO:b 1.

35. The method of claim 13, wherein the polypeptide comprises an amino acid sequence that is at least 95% identical to SEQ ID NO:1.

36. The method of claim 14, wherein the method is performed in the presence of NGF.

37. The method of claim 14, wherein the polypeptide comprises amino acids 1 to 300 and 432–540 of SEQ ID NO:1.

38. The method of claim 14, wherein the polypeptide comprises SEQ ID NO:1.

39. The method of claim 14, wherein the polypeptide comprises an amino acid sequence that is at least 95% identical to SEQ ID NO:1.

40. The method of claim 14, wherein the cell expresses p75.

41. The method of claim 1, wherein the first polypeptide comprises a fusion protein.

42. The method of claim 2, wherein the first polypeptide comprises a fusion protein.

43. The method of claim 11, wherein the polypeptide comprises a fusion protein.

44. The method of claim 13, wherein the polypeptide comprises a fusion protein.

45. The method of claim 14, wherein the polypeptide comprises a fusion protein.

46. The method of claim 1, wherein the second polypeptide comprises a fusion protein.

47. The method of claim 2, wherein the second polypeptide comprises a fusion protein.

48. The method of claim 11, wherein the polypeptide comprises an amino acid sequence encoded by the plasmid deposited in ATCC as Accession number 203037.

49. The method of claim 13, wherein the polypeptide comprises an amino acid sequence encoded by the plasmid deposited in ATCC as Accession number 203037.

50. The method of claim 14, wherein the polypeptide comprises an amino acid sequence encoded by the plasmid deposited in ATCC as Accession number 203037.

* * * * *